US011234676B2

(12) United States Patent
Marcil

(10) Patent No.: US 11,234,676 B2
(45) Date of Patent: Feb. 1, 2022

(54) PROBE HOLDER FOR ULTRASOUND IMAGING DEVICE

(71) Applicant: Elekta LTD., Montreal (CA)

(72) Inventor: Francois Marcil, Montreal (CA)

(73) Assignee: Elekta LTD., Montreal (CA)

(*) Notice: Subject to any disclaimer, the term of this patent is extended or adjusted under 35 U.S.C. 154(b) by 890 days.

(21) Appl. No.: 15/898,498

(22) Filed: Feb. 17, 2018

(65) Prior Publication Data
US 2019/0231305 A1 Aug. 1, 2019

Related U.S. Application Data

(60) Provisional application No. 62/623,463, filed on Jan. 29, 2018.

(51) Int. Cl.
*A61B 8/00* (2006.01)
*A61B 90/57* (2016.01)
(Continued)

(52) U.S. Cl.
CPC ............ *A61B 8/4209* (2013.01); *A61B 8/40* (2013.01); *A61B 90/50* (2016.02); *A61B 90/57* (2016.02);
(Continued)

(58) Field of Classification Search
CPC ......... A61B 8/4209; A61B 8/40; A61B 90/57; A61B 90/50; A61B 2090/0808; A61N 5/1039; A61N 5/1049
See application file for complete search history.

(56) References Cited

U.S. PATENT DOCUMENTS 2,306,031 A 12/1942 Anderson et al.
D264,874 S 6/1982 Augustsson et al.
(Continued)

FOREIGN PATENT DOCUMENTS

CN 110090363 8/2019
WO 2014018983 1/2014

OTHER PUBLICATIONS

Youtube, "Elektra—Electron Boost VeraHD", https://www.youtube.com/watch?v=htoFAd1ALw8, 2015 (Year: 2015).*
(Continued)

*Primary Examiner* — Joanne M Hoffman
(74) *Attorney, Agent, or Firm* — Schwegman Lundberg & Woessner, P.A.; Sanjay Agrawal

(57) ABSTRACT

Systems and methods can include a system for positioning an ultrasound probe proximal to anatomy of a patient on a radiation couch including a substantially planar base including engagement features to directly or indirectly index the substantially planar base to the radiation couch and a centrally located guide extending longitudinally along a top side of the base, a probe holder, configured to be coupled to, to translate longitudinally, and to be user-accessed and user-controlled from within, a central region of the substantially planar base, a clamp, configured to localize the probe holder at a specified location along a translation path in the central region of the substantially planar base, leg supports shaped to accommodate a patient's legs from behind, the pair of leg supports being shaped and arranged to provide a space therebetween that can accommodate an ultrasound probe holder.

10 Claims, 18 Drawing Sheets

(51) Int. Cl.
*A61N 5/10* (2006.01)
*A61B 90/50* (2016.01)
*A61B 90/00* (2016.01)

(52) U.S. Cl.
CPC ......... *A61N 5/1039* (2013.01); *A61N 5/1049* (2013.01); *A61B 2090/0808* (2016.02); *A61B 2090/376* (2016.02); *A61B 2090/378* (2016.02); *A61N 2005/1058* (2013.01); *A61N 2005/1097* (2013.01)

(56) References Cited

U.S. PATENT DOCUMENTS

| | | | |
|---|---|---|---|
| D286,073 S | 10/1986 | Russell | |
| 4,615,516 A | 10/1986 | Stulberg et al. | |
| D310,278 S | 8/1990 | Quinlan | |
| D386,584 S | 11/1997 | Frei | |
| D393,069 S | 3/1998 | Jope | |
| D413,982 S | 9/1999 | Swedberg et al. | |
| D415,281 S | 10/1999 | Swedberg et al. | |
| 5,980,828 A | 11/1999 | Mcclintock et al. | |
| D422,782 S | 4/2000 | Howlett et al. | |
| D462,446 S | 9/2002 | Felix et al. | |
| D463,858 S | 10/2002 | Sherrod et al. | |
| D465,577 S | 11/2002 | Kato et al. | |
| D500,142 S | 12/2004 | Crisanti et al. | |
| D546,956 S | 7/2007 | Buethorn | |
| D550,850 S | 9/2007 | Buethorn | |
| D551,353 S | 9/2007 | Buethorn | |
| D558,889 S | 1/2008 | Doll et al. | |
| D601,250 S | 9/2009 | Haunschild | |
| D625,421 S | 10/2010 | Sharps et al. | |
| D673,689 S | 1/2013 | Pierce et al. | |
| D690,016 S | 9/2013 | Ratner | |
| D709,180 S | 7/2014 | Rummery et al. | |
| D713,967 S | 9/2014 | Adoni | |
| D728,165 S | 4/2015 | Davis | |
| D744,641 S | 12/2015 | Aiken | |
| D780,929 S | 3/2017 | Nurminen | |
| D791,951 S | 7/2017 | Henderson | |
| D794,205 S | 8/2017 | Naber et al. | |
| D800,911 S | 10/2017 | Diemer | |
| D804,045 S | 11/2017 | Epstein | |
| D810,300 S | 2/2018 | Parsons | |
| D814,646 S | 4/2018 | Maloney | |
| D816,833 S | 5/2018 | Parkhurst | |
| 9,980,573 B2 | 5/2018 | Bennetts | |
| D833,623 S | 11/2018 | Naber et al. | |
| D834,205 S | 11/2018 | Ducharme et al. | |
| D837,386 S | 1/2019 | Barber et al. | |
| D837,392 S | 1/2019 | Wanner et al. | |
| D869,666 S | 12/2019 | Michaud | |
| D872,864 S | 1/2020 | Marcil | |
| D885,589 S | 5/2020 | Marcil | |
| D886,300 S | 6/2020 | Marcil | |
| D898,203 S | 10/2020 | Marcil | |
| 10,973,492 B2 | 4/2021 | Marcil | |
| 2004/0030241 A1* | 2/2004 | Green | A61B 5/055 600/422 |
| 2004/0199072 A1* | 10/2004 | Sprouse | A61B 6/12 600/424 |
| 2005/0004457 A1* | 1/2005 | Moilanen | A61B 8/4209 600/437 |
| 2005/0080333 A1* | 4/2005 | Piron | A61B 8/0825 600/417 |
| 2005/0108899 A1 | 5/2005 | Kielt et al. | |
| 2005/0166325 A1* | 8/2005 | Tidwell | A61B 6/0485 5/624 |
| 2005/0222573 A1* | 10/2005 | Branch | A61B 17/154 606/86 R |
| 2006/0142657 A1* | 6/2006 | Quaid | A61B 34/10 600/424 |
| 2007/0161935 A1* | 7/2007 | Torrie | A61G 13/0036 602/32 |
| 2009/0003528 A1* | 1/2009 | Ramraj | A61B 6/527 378/119 |
| 2009/0227874 A1 | 9/2009 | Suri et al. | |
| 2009/0308400 A1* | 12/2009 | Wilson | A61N 5/1049 128/845 |
| 2010/0056914 A1* | 3/2010 | Bruggers | A61B 5/0035 600/439 |
| 2011/0071380 A1* | 3/2011 | Goldenberg | A61B 8/0841 600/411 |
| 2012/0117818 A1 | 5/2012 | Slowik | |
| 2012/0302890 A1* | 11/2012 | Strong | A61B 8/4209 600/459 |
| 2013/0012937 A1* | 1/2013 | Mulier | A61B 18/1477 606/33 |
| 2013/0110019 A1 | 5/2013 | Hopman et al. | |
| 2014/0034800 A1* | 2/2014 | Strong | A61B 8/12 248/299.1 |
| 2014/0107435 A1* | 4/2014 | Sharf | A61B 5/0082 600/301 |
| 2014/0171801 A1* | 6/2014 | Starr | A61B 8/4209 600/459 |
| 2014/0188129 A1* | 7/2014 | Kang | A61G 13/125 606/130 |
| 2014/0298681 A1 | 10/2014 | Epstein | |
| 2015/0190201 A1* | 7/2015 | Olson | A61B 5/6852 606/130 |
| 2015/0196275 A1* | 7/2015 | Kaufman | A61B 8/4477 600/449 |
| 2015/0209599 A1* | 7/2015 | Schlosser | A61B 6/4417 600/427 |
| 2015/0320298 A1* | 11/2015 | Missov | A61B 90/57 600/102 |
| 2015/0342814 A1 | 12/2015 | Terebuh | |
| 2017/0347963 A1* | 12/2017 | Branch | A61B 34/30 |
| 2018/0250183 A1* | 9/2018 | Zwierstra | A61B 5/1127 |
| 2019/0231303 A1 | 8/2019 | Marcil | |
| 2019/0231304 A1 | 8/2019 | Marcil | |
| 2019/0231306 A1 | 8/2019 | Marcil | |
| 2019/0328599 A1* | 10/2019 | Mahoney | A61B 34/20 |
| 2020/0054357 A1 | 2/2020 | Ihatsu | |
| 2020/0405177 A1* | 12/2020 | Wong | A61B 6/0407 |

OTHER PUBLICATIONS

"U.S. Appl. No. 29/635,179, Final Office Action dated Mar. 27, 2020", 7 pgs.

"U.S. Appl. No. 29/635,185, Notice of Allowance dated Mar. 27, 2020", 7 pgs.

"U.S. Appl. No. 29/635,186, Notice of Allowance dated Apr. 3, 2020", 8 pgs.

"U.S. Appl. No. 29/635,185, PTO Response to Rule 312 Communication dated Apr. 29, 2020", 2 pgs.

"U.S. Appl. No. 29/635,186, Corrected Notice of Allowability dated Apr. 29, 2020", 2 pgs.

"U.S. Appl. No. 15/898,503, Non Final Office Action dated Jun. 11, 2020", 9 pgs.

"U.S. Appl. No. 29/635,179, Response filed Jun. 24, 2020 to Final Office Action dated Mar. 27, 2020", 4 pgs.

"U.S. Appl. No. 29/635,179, Notice of Allowance dated Jul. 23, 2020", 8 pgs.

"Application Serial No. 15/898,503, Response filed Oct. 13, 2020 to Non Final Office Action dated Jun. 11, 2020", 9 pgs.

"U.S. Appl. No. 15/898,486, Non Final Office Action dated Mar. 2, 2021", 12 pgs.

"Chinese Application Serial No. 201910080350.6, Notification on Correction of Deficiencies dated Mar. 12, 2019", w Concise Statement of Relevance, 2 pg.

"U.S. Appl. No. 29/635,179, Non Final Office Action dated Apr. 19, 2019", 13 pgs.

"U.S. Appl. No. 29 635,182, Non Final Office Action dated Apr. 26, 2019", 11 pgs.

"RayBoards for Butterfly Masks with L-Profiles", [Online] Retrieved from the Internet :https: www.bcc.taipeiRTproducts product_pp121a. html, (accessed Mar. 19, 2019), 1.

(56) References Cited

OTHER PUBLICATIONS

"U.S. Appl. No. 29/635,185, Non Final Office Action dated May 16, 2019", 16 pgs.

"U.S. Appl. No. 29/635,186, Non Final Office Action dated May 16, 2019", 12 pgs.

"European Application Serial No. 19153998.0, Extended European Search Report dated Jun. 28, 2019", 11 pgs.

"Zephyr Patient Positioning and Transfer Systems", Orfit Industries, Retrieved from the Internet:URL:https: www.orfit.com radiation-oncology products zephyrpatient-positioning-and-transfer-systems, (May 30, 2017), 2 pgs.

"U.S. Appl. No. 29/635,179, Response filed Jul. 19, 2019 to Non-Final Office Action dated Apr. 19, 2019", 6 pgs.

"U.S. Appl. No. 29/635,182, Response filed Aug. 12, 2019 to Non Final Office Action dated Apr. 26, 2019", 5 pgs.

"U.S. Appl. No. 29/635,185, Response filed Aug. 14, 2019 to Non Final Office Action dated May 16, 2019", 5 pgs.

"U.S. Appl. No. 29/635,186, Response filed Aug. 14, 2019 to Non Final Office Action dated May 16, 2019", 7 pgs.

"U.S. Appl. No. 29/635,182, Notice of Allowance dated Sep. 3, 2019", 7 pgs.

Damps, Saskia M, "The Use of Ultrasound Imaging in the External Beam Radiotherapy Workflow of Prostate Cancer Patients", Biomed Research International, vol, (Jan. 1, 2018), 1-16.

Elekta, "Prostate Intra-Fractional Motion Management", Youtube, Retrieved from the Internet:URL:https: www.youtube.com watch?v=Qr8z5ELbQJw, (Feb. 3, 2016), 1 pg.

Elekta, "Clarity for Prostate Monitoring", Youtube, Retrieved from the Internet:URL:https: www.youtube.com watch?time_continue=35andv=htoFAd1 ALw8, (Sep. 22, 2015), 1 pg.

Lachaine, Martin, "Intrafractional Prostate Motion Management With The Clarity Autoscan System", Medical Physics International Journal, (Jan. 1, 2013), 72.

Zephyr, "Image Guided Braciiylfterapy with Zephyr MDR", Youtube, Retrieved from the Internet:URL:https: www.youtube.com watch?time_continue=111andv=SaKI8ceQirY, (May 30, 2017), 1 pg.

"U.S. Appl. No. 29/635,179, Non Final Office Action dated Oct. 10, 2019", 15 pgs.

"U.S. Appl. No. 29/635,186, Final Office Action dated Nov. 5, 2019", 7 pgs.

"U.S. Appl. No. 29/635,185, Final Office Action dated Nov. 21, 2019", 8 pgs.

"U.S. Appl. No. 29/635,182, Corrected Notice of Allowability dated Dec. 11, 2019", 4 pgs.

"U.S. Appl. No. 29/635,179, Response filed Jan. 6, 2020 to Non Final Office Action dated Oct. 10, 2019", 5 pgs.

"European Application Serial No. 19153998.0, Response filed Jan. 31, 2020 to Extended European Search Report dated Jun. 28, 2019", 11 pgs.

"U.S. Appl. No. 29/635,186, Response filed Feb. 3, 2020 to Final Office Action Dated Nov. 5, 2019", 6 pgs.

"U.S. Appl. No. 29/635,185, Response filed Feb. 17, 2020 to Final Office Action dated Nov. 21, 2019", 5 pgs.

Bionix Radiation Therapy, "Comfort Hold Foot Positioner RT-6030-30-03", [Online]. Retrieved from the Internet: <URL: www.BionixRT.com>, 2 pgs.

CDR Systems, "CDR Systems Precision Positioning Systems", [Online]. Retrieved from the internet: <URL:www.cdrsys.ca>, 58 pgs.

Klarity, "R634-LCF Leg Positioner Set-Up", [Online]. Retrieved from the Internet:<URL: www.klaritymedical.com>, 1 pg.

"U.S. Appl. No. 15/898,486, Response filed Feb. 9, 2021 to Restriction Requirement dated Jan. 4, 2021", 5 pgs.

"U.S. Appl. No. 15/898,486, Restriction Requirement dated Jan. 4, 2021", 6 pgs.

"U.S. Appl. No. 15/898,495, Response filed Feb. 9, 2021 to Restriction Requirement dated Dec. 14, 2020", 6 pgs.

"U.S. Appl. No. 15/898,495, Restriction Requirement dated Dec. 14, 2020", 6 pgs.

"U.S. Appl. No. 15/898,503, Notice of Allowance dated Dec. 18, 2020", 8 pgs.

"U.S. Appl. No. 15/898,486, Final Office Action dated Jul. 21, 2021", 8 pgs.

"U.S. Appl. No. 15/898,486, Response filed Jun. 2, 2021 to Non Final Office Action dated Mar. 2, 2021", 15 pgs.

"U.S. Appl. No. 15/898,495, Final Office Action dated Aug. 19, 2021", 8 pgs.

"U.S. Appl. No. 15/898,495, Non Final Office Action dated Apr. 28, 2021", 18 pgs.

"U.S. Appl. No. 15/898,495, Response filed Jul. 28, 2021 to Non Final Office Action dated Apr. 28, 2021", 13 pgs.

"U.S. Appl. No. 15/898,503, Supplemental Notice of Allowability dated Mar. 19, 2021", 3 pgs.

Elekta, "Elect Clarity", YouTube, [Online] Retrieved from the internet: <https://www.youtube.com/watch?v=Qr8z5ELbQJw> (Year: 2016), (2016).

"U.S. Appl. No. 15/898,486, Notice of Allowance dated Oct. 4, 2021", 8 pgs.

"U.S. Appl. No. 15/898,495, Response filed Oct. 4, 2021 to Final Office Action dated Aug. 19, 2021", 10 pgs.

"U.S. Appl. No. 15/898,486, Response filed Sep. 16, 2021 to Final Office Action dated Jul. 21, 2021", 10 pgs.

"U.S. Appl. No. 15/898,495, Advisory Action dated Nov. 18, 2021", 5 pgs.

\* cited by examiner

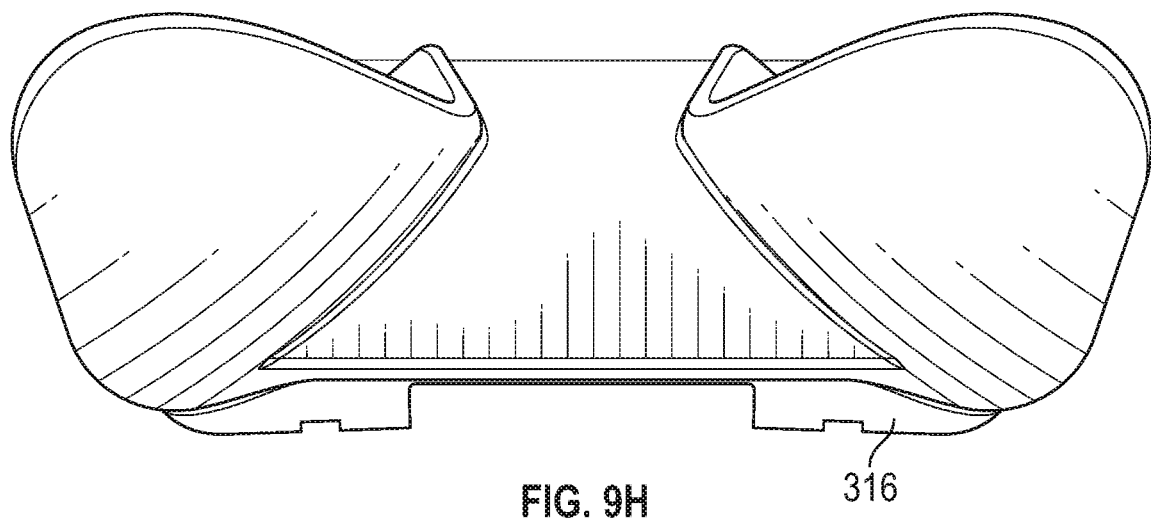
FIG. 9H   316
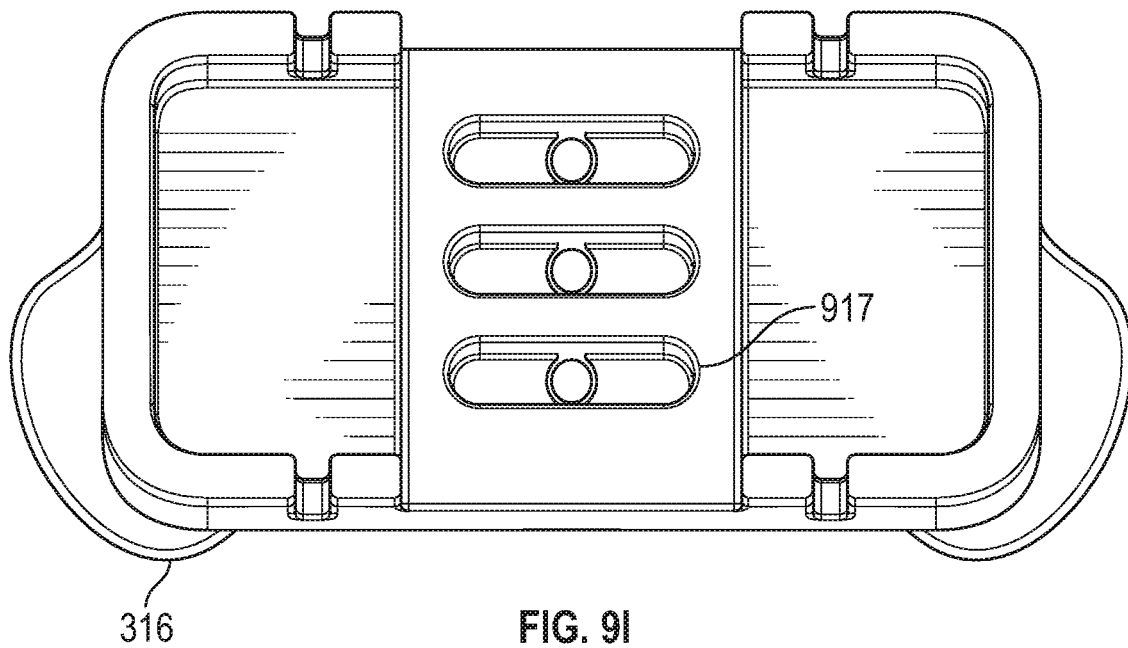
316   FIG. 9I

PROBE HOLDER FOR ULTRASOUND IMAGING DEVICE

CLAIM OF PRIORITY

This patent application claims the benefit of priority of U.S. Provisional Patent Application Ser. No. 62/623,463, filed on Jan. 29, 2018, naming Francois Marcil as inventor, and entitled ULTRASOUND POSITIONING DEVICE, which is hereby incorporated by reference herein in its entirety.

TECHNICAL FIELD

Embodiments of the present subject matter pertain generally to a system for positioning an ultrasound device proximal to an anatomy of a patient.

Overview

Radiotherapy is used to treat cancers and other ailments in mammalian (e.g., human and animal) tissue. An example of radiotherapy is provided using a linear accelerator (LINAC), by which a target (e.g., a tumor) is irradiated by high-energy particles in a radiation beam (e.g., electrons, photons, ions, or the like). In an example of LINAC-based radiation treatment, multiple radiation beams are directed toward the target from different angles. The placement and dose of the radiation beam should be accurately controlled to ensure that the tumor receives the prescribed radiation, and the placement of the beam should be such as to minimize damage to the surrounding healthy tissue, which can be called the organ(s) at risk (OARs).

To prevent OARs from the severe collateral damage that can be caused by the radiation beams, the doses received by these OARs should be limited to a certain level. Such limitations on the doses received by the OARs, sometimes called constraints, need to be satisfied during radiation treatment planning.

Treatment planning is a process involving determination of one or more specific radiotherapy parameters (e.g., radiation beam angles, radiation intensity level at each angle, etc.) for implementing a treatment goal under the constraints. A typical treatment planning process includes delineating one or more targets and one or more OARs from a medical image of the patient, specifying radiation beam angles, or a range of angles in the case of an arc plan, and determining an aperture shape or shapes and radiation intensity levels for each shape at each beam angle. Ultrasound imaging is one type of medical imaging that can be used during treatment planning (e.g., 2D ultrasound, 3D ultrasound, 4D ultrasound). The ultrasound imaging can also be used during the radiation treatment such as to determine in real time if targets or OARs have moved.

In certain radiation treatment systems, a patient can be positioned on a radiation couch and an ultrasound probe can be positioned proximal to anatomy of a patient, such as to acquire ultrasound images of the patient anatomy for treatment planning or during the radiation treatment of the patient.

The inventors have recognized, among other things, that the process of positioning an ultrasound probe can be greatly improved by providing a radiation treatment system in which the ultrasound probe can be indexed to a radiation couch and additionally can be centrally accessed and positioned while a patient is on the radiation couch.

In an aspect, the disclosure can feature an overlay for providing a movable interface between an ultrasound probe holder and a couch for radiotherapy. The overlay can include a substantially planar base including a top side. The overlay can also include a centrally located elongated guide extending longitudinally along the top side of the base, such as to guide translational movement of the ultrasound probe holder along a longitudinal axis of the overlay. The elongated guide can include a longitudinal groove arranged to guide the ultrasound probe holder during translational movement along the longitudinal axis of the overlay. The elongated guide can include a pair of rails including respective longitudinal grooves centrally facing each other and arranged to guide the ultrasound probe holder during translational movement along a longitudinal axis of the overlay. The elongated guide can include a pair of rails including respective longitudinal grooves, outwardly facing away from each other and arranged, such as to engage at least one patient support cushion. The overlay can also include indexed engagement features that can engage directly or indirectly with the couch, a handle located at a first inferior end of the base of the overlay, and one or more glides located on a bottom side of the base at an opposing second superior end of the base of the overlay. The indexed engagement features can be arranged to engage with an indexing bar that engages with the couch. A first inferior end of the elongated guide can include a unidirectional entry and capture member, such as to allow entry and engagement of a portion of the probe holder into the groove and to inhibit exit from the groove without user-disengagement of the unidirectional entry and capture member, and wherein a second superior end of the elongated guide can include a stop to prevent exit of the probe holder from the groove. The base can include leg support base regions extending in laterally opposing directions from the centrally located elongated guide, the leg support base regions configured to provide indexed longitudinal and lateral placement of respective knee support cushions and to provide adjustable longitudinal placement of respective foot support cushions. A pair of outwardly facing longitudinal grooves can be configured to provide the adjustable longitudinal placement of the respective foot cushions. The overlay can also include a plurality of apertures at the second superior end of the base, the pair of apertures configured, such as to provide a handle for providing coarse positioning of the base with respect to the couch.

In an aspect, the disclosure can feature an overlay for providing a movable indexed adjustable interface between a subject and a radiation couch. The overlay can include a substantially planar base including a top side and a bottom side. The overlay can also include a handle located on a top side at an inferior longitudinal end of the base. The overlay can also include one or more glides located on a bottom side at an opposing superior longitudinal end of the base. The overlay can also include indexed engagement features, such as to engage directly or indirectly with the radiation couch. The indexed engagement features can be arranged to engage with an indexing bar that engages with the radiation couch. The one or more glides can include a first set of glides located on the bottom side at the inferior longitudinal end of the base, the first set of glides being configured to provide resistance to movement of the base along a longitudinal direction and a second set of longitudinal glides located on bottom of the superior longitudinal end of the base, the second set of glides being configured to permit movement of the base along the longitudinal direction.

In an aspect, the disclosure can feature a method of using an overlay to index a position of an ultrasound probe holder to a radiation couch, the overlay including a substantially planar base including a top side, and including a centrally located elongated guide extending longitudinally along the top side of the base to guide translational movement of the ultrasound probe holder along a longitudinal axis of the overlay. The method can include positioning the overlay at an indexed position on a radiation couch. The method can also include guiding translational movement of the ultrasound probe holder along a longitudinal axis of the overlay from within a central region of the overlay. The method can also include guiding translational movement of the ultrasound probe holder from within the central region of the overlay using a longitudinal groove along the longitudinal axis of the overlay. The method can also include guiding translational movement of the ultrasound probe holder from within the central region of the overlay using a pair of rails including respective longitudinal grooves centrally facing each other along a longitudinal axis of the overlay. The method can also include engaging at least one patient support cushion using respective longitudinal grooves, outwardly facing away from each other. The method can also include positioning the overlay without engaging indexed engagement features using a handle located at a first inferior end of the base of the overlay, and one or more glides, located on a bottom side of the base at an opposing superior second end of the base of the overlay and then placing the overlay into engagement with one or more of the indexed engagement features. Providing indexed engagement to a radiation couch can include using an indexing bar that engages with the radiation couch and with the overlay.

In an aspect, the disclosure can feature a probe holder for positioning an ultrasound probe. The probe holder can include a probe holder body, configured to be coupled to, to translate longitudinally within, and to be user-accessed and user-controlled from within, a central region of a radiation couch or overlay thereupon, the central region being located between lateral regions that are arranged to be underlying a subject's legs. The probe holder can also include a clamp, configured to localize the probe holder at a specified location along a translation path in the central region. The probe holder can also include a rotatably-actuated clamp located within a central portion of the probe holder body, the clamp being configured to increase a frictional force between the probe holder body and the overlay to localize the probe holder at a specified location along a translation path in the central region. The probe holder can also include transversely outwardly facing protrusions aligned along a longitudinal direction, the outwardly facing protrusions configured to interface with corresponding longitudinal grooves of the overlay to provide for adjustment of the probe body along a longitudinal direction. The probe holder can also include transversely outwardly facing hemispherical protrusions having a semi-circular cross-section aligned along a longitudinal direction, the outwardly facing protrusions configured to interface with corresponding longitudinal v-grooves of the overlay to provide for adjustment of the probe body along a longitudinal direction. The probe holder can also include a retractable flap configured to hold the ultrasound probe in place upon the ultrasound probe engaging with the probe holder and release the ultrasound probe upon being actuated by a user. The probe holder can also include a rotatable knob located within the central portion of the probe holder body, the rotatable knob being configured to apply a force to the overlay when engaging a relatively elevated portion of a disc below the rotatable knob to provide an outwardly facing protrusion. The rotatable knob can be configured to decrease a clearance between outwardly facing protrusions of the probe holder and corresponding longitudinal grooves of the overlay in response to a rotation in a first direction. The rotatable knob can be configured to increase a clearance between outwardly facing protrusions of the probe holder and corresponding longitudinal grooves of the overlay in response to further rotation in the first direction. The rotatable knob can be configured to increase a clearance between outwardly facing protrusions of the probe holder and corresponding longitudinal grooves of the overlay in response to a further rotation in the first direction or a rotation in a second direction opposite to the first direction. The probe holder can also include a rotatable, longitudinally aligned member configured to longitudinally translate the ultrasound probe with respect to the overlay and to be user-accessed and user-controlled from within, a central region of a radiation couch or overlay thereupon. The rotatable, longitudinally aligned member is located on a side opposite of the ultrasound probe to provide for access to the rotatable, longitudinally aligned member and is located to be user-accessed and user-controlled from within, a central region of a radiation couch or overlay thereupon.

In an aspect, the disclosure can feature a method for using a probe holder for positioning an ultrasound probe at a specified location along a longitudinal translation path within a central region of a radiation couch or overlay thereupon, the central region being located between lateral regions that are arranged to be underlying a patient's legs. The method can include user-accessing and user-controlling, from within the central region, a probe holder for translating the probe longitudinally toward and away from a portion of the patient. The method can also include clamping, from within the central region, the probe holder at a specified location along the translation path in the central region. The method can also include rotating an actuator on a clamp to increase a frictional force associated with the probe holder. Translating the probe longitudinally can include using transversely outwardly facing protrusions to interface with corresponding longitudinal grooves. Clamping can include reducing a clearance within a groove. The method can also include automatically engaging or retaining the probe upon insertion onto the translation path and requiring user-activated release of the probe upon removal from the translation path. The clamping can include rotating a knob to engage a relatively elevated portion of a disc having a variable height. The method can also include unclamping, from within the central region, the probe holder, the unclamping comprising rotating the knob to engage a relatively lower portion of the disc having a variable height. The unclamping can include rotating the knob in an opposite direction as the rotating for clamping. The method can also include fine-adjusting a longitudinal position of the probe holder along the translation path using a separate actuation from a gross-adjusting of the longitudinal position of the probe holder along the translation path. The fine-adjusting can be accessible from a side of the probe holder configured to be inferior to the patient.

In an aspect, the disclosure can feature supports for a lower body of a patient. The supports can include a pair of separate knee supports, each individual knee support including a portion shaped to accommodate a patient's knee from behind the knee, the pair of knee supports being shaped and arranged to provide a space therebetween that can accommodate an ultrasound probe holder. The supports can also include a pair of knee supports having a recessed portion corresponding to a raised mounting portion of an overlay, wherein a recessed portion of each individual knee support includes indexed engagement features for engaging a corresponding mounting portion of the overlay. The supports can also include a pair of knee supports having a protruding portion corresponding to a recessed portion of an overlay, wherein a protruding portion of each individual knee support includes indexed engagement features for engaging a corresponding recessed portion of the overlay. The space between the pair of knee supports can allow for access to a patient's perineum. The supports can also include a pair of separate ankle supports including a portion shaped to accommodate a patient's ankles from behind and a lateral slide for engaging a corresponding feature of an overlay for a radiation couch. The supports can also include a booster shaped to be inserted between an individual one of the knee supports and the overlay to provide an increased height of the knee support with respect to the overlay. The booster can be shaped to be inserted between an ankle support cushion and the overlay to provide an increased height of the ankle support cushion with respect to the overlay. The pair of ankle supports can include a recessed portion on a bottom side of an individual one of the ankle supports to provide clearance for an ultrasound probe holder.

In an aspect, the disclosure can feature a method for supporting a lower body of a patient. The method can include supporting, on a first knee support on a radiation couch or an overlay thereupon, a first knee of a patient from behind the first knee. The method can also include supporting, on a second knee support on the radiation couch or on the overlay thereupon, a second knee of the patient from behind the second knee. The method can also include providing access to a patient via a probe holder in a central region formed by the first and second knee supports being placed in lateral regions on opposing sides. The method can also include placing the first and second knee supports on the radiation couch or the overlay thereupon using an indexing engagement feature of each individual knee support. The method can also include providing access to the patient's perineum in a space between the first and second knee supports. The method can also include separately supporting, on an ankle support on a radiation couch or an overlay thereupon, an ankle of the patient from behind the ankle, and allowing longitudinal adjustment of the ankle support along a longitudinal track. The method can also include inserting a booster between at least one of the first or second knee supports and the overlay to provide an increased height of the at least one of the first or second knee support with respect to the overlay. The method can also include inserting a booster between the ankle support and the overlay to provide an increased height of the ankle support with respect to the overlay. An individual instance of the booster can adapted to be used selectably with the first or second knee supports and with the ankle support.

In an aspect, the disclosure can feature a method of supporting a lower body of a patient. The method can include supporting a patient's knees using a knee support shaped and arranged to provide a space therebetween that can accommodate an ultrasound probe holder. The method can also include indexing the knee support to a raised mounting portion of an overlay using a recessed portion of the knee support. The method can also include providing access to the patient's perineum via the space between the knee support. The method can also include adjusting a longitudinal position of a pair of ankle supports in a longitudinal direction along an exterior groove of an overlay. The method can also include inserting a booster between the knee supports and an overlay to provide an increased height of the knee supports with respect to the overlay. The method can also include inserting a booster between the ankle supports and the overlay to provide an increased height of the ankle supports with respect to the overlay.

In an aspect, the disclosure can feature a system for positioning an ultrasound probe proximal to anatomy of a patient on a radiation couch. The system can include a substantially planar base including engagement features to directly or indirectly index the substantially planar base to the radiation couch and a centrally located guide extending longitudinally along a top side of the base. The system can also include a probe holder, configured to be coupled to, to translate longitudinally, and to be user-accessed and user-controlled from within, a central region of the substantially planar base. The system can also include a clamp, configured to localize the probe holder at a specified location along a translation path in the central region of the substantially planar base. The system can also include leg supports shaped to accommodate a patient's legs from behind, the pair of leg supports being shaped and arranged to provide a space therebetween that can accommodate an ultrasound probe holder. The system can also include an indexing bar for providing a transversely aligned interface between the substantially planar base and the radiation couch, the indexing bar including protrusions on a bottom side for engaging with slots in the radiation couch and protrusions on a top side for engaging with the substantially planar base. The centrally located guide can include a pair of rails including respective longitudinal grooves centrally facing each other and arranged to guide the probe holder during translational movement along a longitudinal axis of the base and the centrally located guide can include a pair of rails including respective longitudinal grooves, outwardly facing away from each other and arranged to engage at least one patient support cushion. The system can also include a pair of ankle supports including a portion shaped to accommodate the patient's ankles and latterly inwardly facing protrusions for contacting at least one outwardly facing groove of the centrally located guide, the inwardly facing protrusions capable of allowing adjustment of a longitudinal position of the pair of ankle supports. The radiation couch can include a scale capable of indexing the indexing bar and the substantially planar base includes a scale capable of indexing the probe holder and ankle supports. The system can also include a clamp located within a hollow central portion of the probe holder, the clamp being configured to increase a frictional force between the probe holder and the substantially planar base. The system can also include a rotatable knob located within a central portion of the probe holder body, the rotatable knob being configured to apply a force to the substantially planar base when engaging a relatively elevated portion of a disc below the rotatable knob to provide an outwardly facing protrusion.

In an aspect, the disclosure can feature a method of positioning an ultrasound probe proximal to anatomy of a patient on a couch for radiotherapy. The method can include positioning an indexing bar on the radiation couch at a marked position of the couch. The method can also include positioning an overlay with respect to the indexing bar at a first marked position of the overlay. The method can also include positioning the patient on the couch and overlay. The method can also include attaching a pair of knee cushions to a raised portion of the overlay. The method can also include adjusting a position of the overlay to position the overlay with respect to the indexing bar at a second marked position of the overlay. The method can also include coupling a probe holder to a central guide region of the overlay. The method can also include coupling an ultrasound probe to the probe holder in a central guide region of the overlay. The method can also include adjusting a position of a pair of ankle cushions to provide support to the patient's ankles. The method can also include longitudinally adjusting a position of the probe holder to bring an ultrasound probe into proximity to a perineum of the patient. The method can also include recording the marked position of the radiation couch and the marked position of the overlay. The method can also include removing the overlay and the indexing bar from the radiation couch. The method can also include using the recorded marked positions to position the indexing bar and overlay. The method can also include accessing and controlling the probe holder from within a central region of the radiation couch to adjust a longitudinal position of the probe holder. The method can also include rotating an actuator located within a central region of the probe holder to increase a frictional force between outwardly facing protrusions of the probe holder and corresponding longitudinal grooves of the overlay in response to a rotation in a first direction. The method can also include rotating an actuator located within a central region of the probe holder to increase a frictional force associated with the probe holder. The method can also include individually adjusting the pair of knee cushions to provide support to a back of the patient's knees. The method can also include automatically engaging or retaining the ultrasound probe upon insertion onto a translation path and requiring user-activated release of the ultrasound probe upon removal from the translation path. The method can also include guiding translational movement of the probe holder from within the central guide region of the overlay using a longitudinal groove along a longitudinal axis of the overlay. The method can also include engaging the pair of ankle cushions using respective longitudinal grooves of the overlay, outwardly facing away from each other. The method can also include positioning the overlay using a handle located at a first end of the overlay, and one or more glides, located on a bottom side of the overlay on an opposing second end of the overlay; and then placing the overlay into engagement with one or more of indexed engagement features.

The above overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIGS. 9A-9I illustrate examples of a patient support cushions.

DETAILED DESCRIPTION

In certain radiation treatment systems, a patient can be positioned on a surface such as can be provided by radiation couch, and an ultrasound probe can be positioned with respect to anatomy of a patient, such as to acquire ultrasound images of the patient anatomy for treatment planning or during the radiation treatment of the patient. The ultrasound probe may have to be repositioned many times over the course of radiation treatment planning or radiation treatment.

The present inventor has recognized, among other things, that the process of positioning an ultrasound probe can be greatly improved by providing a radiation treatment system in which the ultrasound probe can be indexed with respect to a radiation couch and additionally can be centrally accessed and positioned while a patient is on the radiation couch, such as to improve the speed and accuracy at which the patient and ultrasound probe can be positioned, such as can improve patient workflows (e.g., allow for each patient to be treated in less time and with more accuracy). Accessing the ultrasound probe from just one side of the radiation couch may be awkward or inefficient, while central access from either side of the radiation couch can help provide improved ease-of-access and use, which can make a treatment planning session or treatment procedure more efficient.

Figure 1:
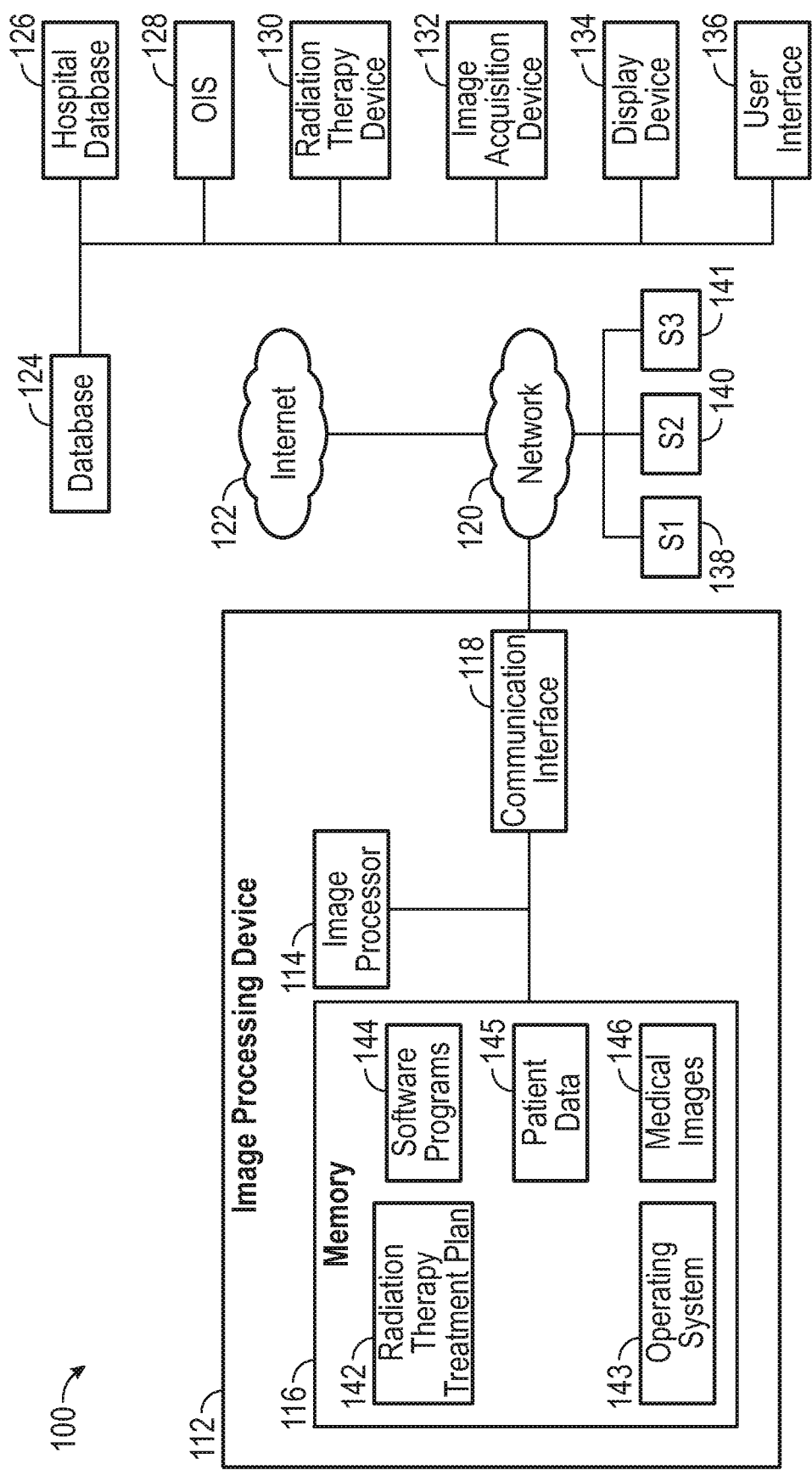
FIG. 1 illustrates an example of portions of a radiotherapy system, according to some embodiments of the present disclosure.

FIG. 1 illustrates an example of a radiotherapy system 100 for providing radiation therapy to a patient. The radiotherapy system 100 can include or be coupled to an image processing device, 112. The image processing device 112 may be connected to one or more of a local or a wide area communications or other network 120. For example, the network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, or a user interface 136. The image processing device 112 can be configured to be used to generate one or more radiation therapy treatment plans 142 to be used by the radiation therapy device 130.

The image processing device 112 may include a memory device 116, a processor 114 circuit and a communication interface 118. The memory device 116 may store computer-executable instructions, such as an operating system 143, one or more radiation therapy treatment plans 142 (e.g., original treatment plans, adapted treatment plans, or the like), software programs 144 (e.g., artificial intelligence, deep learning, neural networks, radiotherapy treatment plan software), or any other computer-executable instructions to be executed by the processor 114. In an embodiment, the software programs 144 may convert medical images of one format (e.g., MRI) to another format (e.g., CT) such as by producing one or more synthetic images, such as a pseudo- CT image. For instance, the software programs 144 may include image processing programs such as to train a predictive model for converting a medial image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (which can also be represented as an image) so that corresponding image voxels and dose voxels are associated appropriately by the network. In yet another embodiment, the software programs 144 may substitute one or more functions of the patient images such as signed distance functions or processed versions of the images that emphasize some aspect of the image information. Such functions may emphasize edges or differences in voxel textures, or any other structural aspect useful to neural network learning. In another embodiment, the software programs 144 may substitute one or more functions of the dose distribution that can emphasize some aspect of the dose information. Such functions may emphasize steep gradients around the target, or any other structural aspect useful to neural network learning. The memory device 116 may store data, including medical images 146, patient data 145, and other data useful to create and implement a radiation therapy treatment plan 142.

In addition to the memory 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., dose-volume histogram (DVH) information: or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image: such software 144 when executed may train a boundary detector, or utilize a shape dictionary.

The processor 114 may be a processing device, and may include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium™ family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core circuit design or a plurality of processors each having a multi-core design. The processor 114 can execute sequences of computer program instructions, stored in memory 116, to perform various operations, processes, methods that will be explained in greater detail below.

The memory device 116 can store medical images 146. In some embodiments, the medical images 146 may include one or more MRI image (e.g., 2D MRI, 3D MR, 2D streaming MRI, 4D MRI, 4D volumetric MRI, 4D cine MRI, etc.), functional MRI images (e.g., fMRI, DCE-MRI, diffusion MRI). Computed Tomography (CT) images (e.g., 2D CT, Cone beam CT, 3D CT, 4D CT), ultrasound images (e.g., 2D ultrasound. 3D ultrasound, 4D ultrasound), Positron Emission Tomography (PET) images. X-ray images, fluoroscopic images, radiotherapy portal images, Single-Photo Emission Computed Tomography (SPECT) images, computer generated synthetic images (e.g., pseudo-CT images) and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 146 may be received and stored in any type of data or any type of format that the image processing device 112 may use to perform operations consistent with the disclosed embodiments. The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory 116. The Communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtain CT images (e.g., medical images 146). In addition, network 120 may be connected to internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 such as to be accessed by the processor 114, as required.

The image processing device 112 may communicate with database 124 through network 120 to send/receive a plurality of various types of data stored on database 124. For example, database 124 may include machine data that is information associated with a radiation therapy device 130, image acquisition device 132, or other machines relevant to radiotherapy. Machine data information may include radiation beam size, arc placement, beam on and off time duration, machine parameters, segments, multi-leaf collimator (MLC) configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 114 may communicate with database 124 to read images into memory 116 or store images from memory 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 124 received from image acquisition device 132. Database 124 may store data to be used by the image processor 114 when executing software program 144, or when creating radiation therapy treatment plans 142. Database 124 may store the data produced by the trained neural network including the network parameters constituting the model learned by the network and the resulting predicted data. The image processing device 112 may receive the imaging data 146 (e.g., 2D MRI slice images, CT images, 2D Fluoroscopy images. X-ray images, 3DMRI images, 4D MRI images, etc.) either from the database 124, the radiation therapy device 130 (e.g., a MRI-Linac), and or the image acquisition device 132 to generate a treatment plan 142.

In an embodiment, the radiotherapy system 100 can include an image acquisition device 132 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 132 can be stored within database 124 as either imaging data and/or test data. By way of example, the images acquired by the imaging acquisition device 132 can be also stored by the image processing device 112, as medical image data 146 in memory 116.

In an embodiment, for example, the image acquisition device 132 may be integrated with the radiation therapy device 130 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "near real-time" while a patient is undergoing radiation therapy treatment, for example, when using the radiation therapy device 130. "Near real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as beam angles, dose-histogram-volume information, the number of radiation beams to be used during therapy, the dose per beam, or the like.

The image processor 114 may generate the radiation therapy treatment plan 142 by using software programs 144 such as treatment planning software, such as Monaco®, manufactured by Elekta AB of Stockholm, Sweden. In order to generate the radiation therapy treatment plans 142, the image processor 114 may communicate with the image acquisition device 132 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software. ABAS™, manufactured by Elekta AB of Stockholm. Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR: defining 95% of dose to the target tumor; defining that the spinal cord, brain stein, and optic structures receive ≤45 Gy, ≤55 Gy and ≤54 Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer, e.g., Apple iPad®, Lenovo Thinkpad®, Samsung Galaxy®, etc.

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, the image acquisition device 132 could be implemented as a virtual machine Given the processing power, memory, and computational capability available, the entire radiotherapy system 100 could be implemented as a virtual machine.

Figure 2:
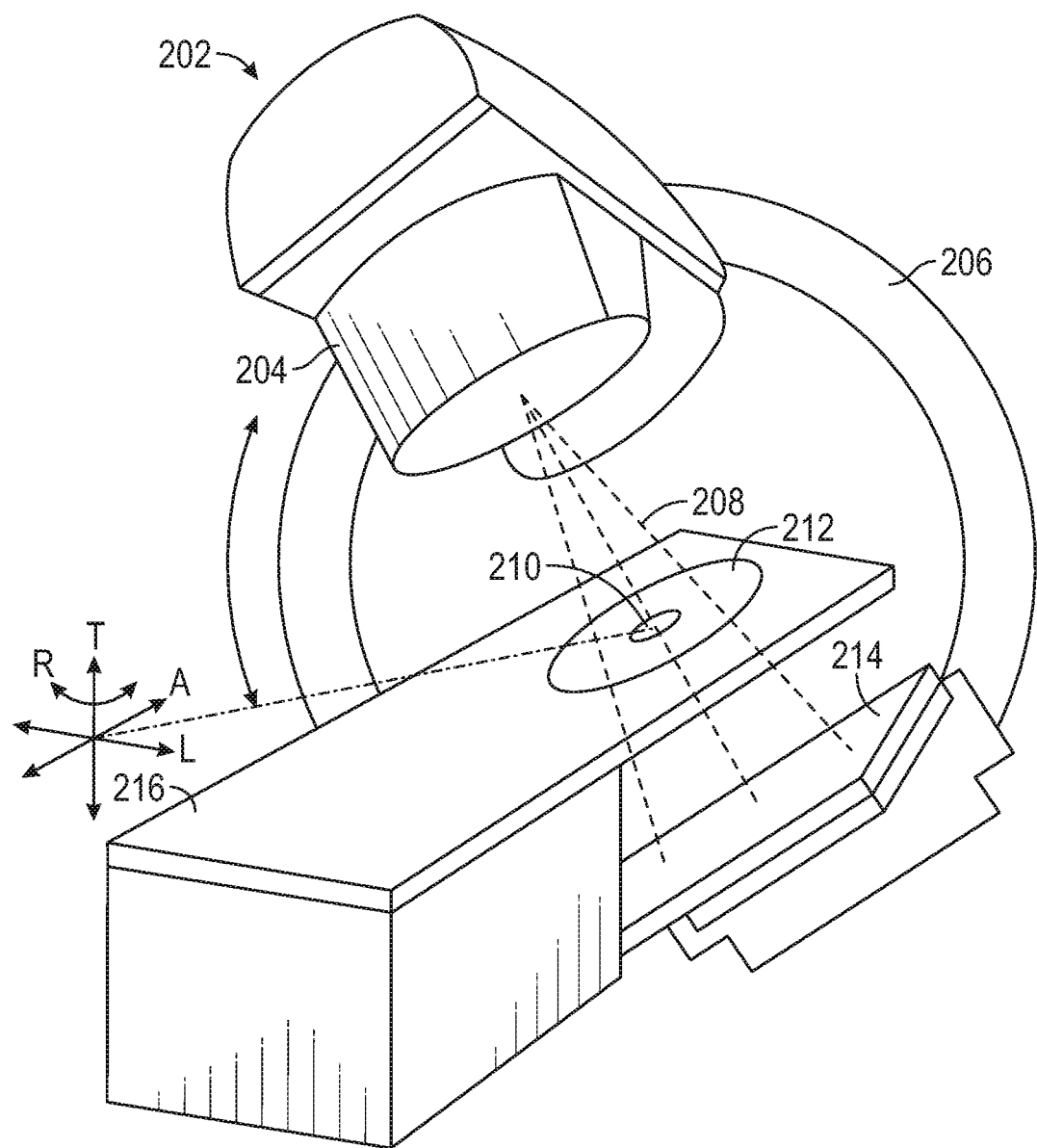
FIG. 2 illustrates an example of portions of radiation therapy system that can include radiation therapy output configured to provide a therapy beam.

FIG. 2 illustrates an example of portions of radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

In FIG. 2, a patient can be positioned in a region 212, supported by the treatment couch 216 to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into or located within the treatment area. In an embodiment, gantry 206 may be continuously rotatable around couch 216 when the couch 216 is inserted into or located within the treatment area. In another embodiment, gantry 206 may rotate to a predetermined or specified position when the couch 216 is inserted into the treatment area. For example, the gantry 206 can be configured to rotate the therapy output 204 around an axis ("A") that can point in a longitudinal direction. Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy such as portal imaging. The control circuitry of radiotherapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

FIG. 2 generally illustrates an embodiment of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient. In another embodiment, a radiation therapy device can be a combination of a linear accelerator and an image acquisition device. In some embodiments, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Figure 3A:
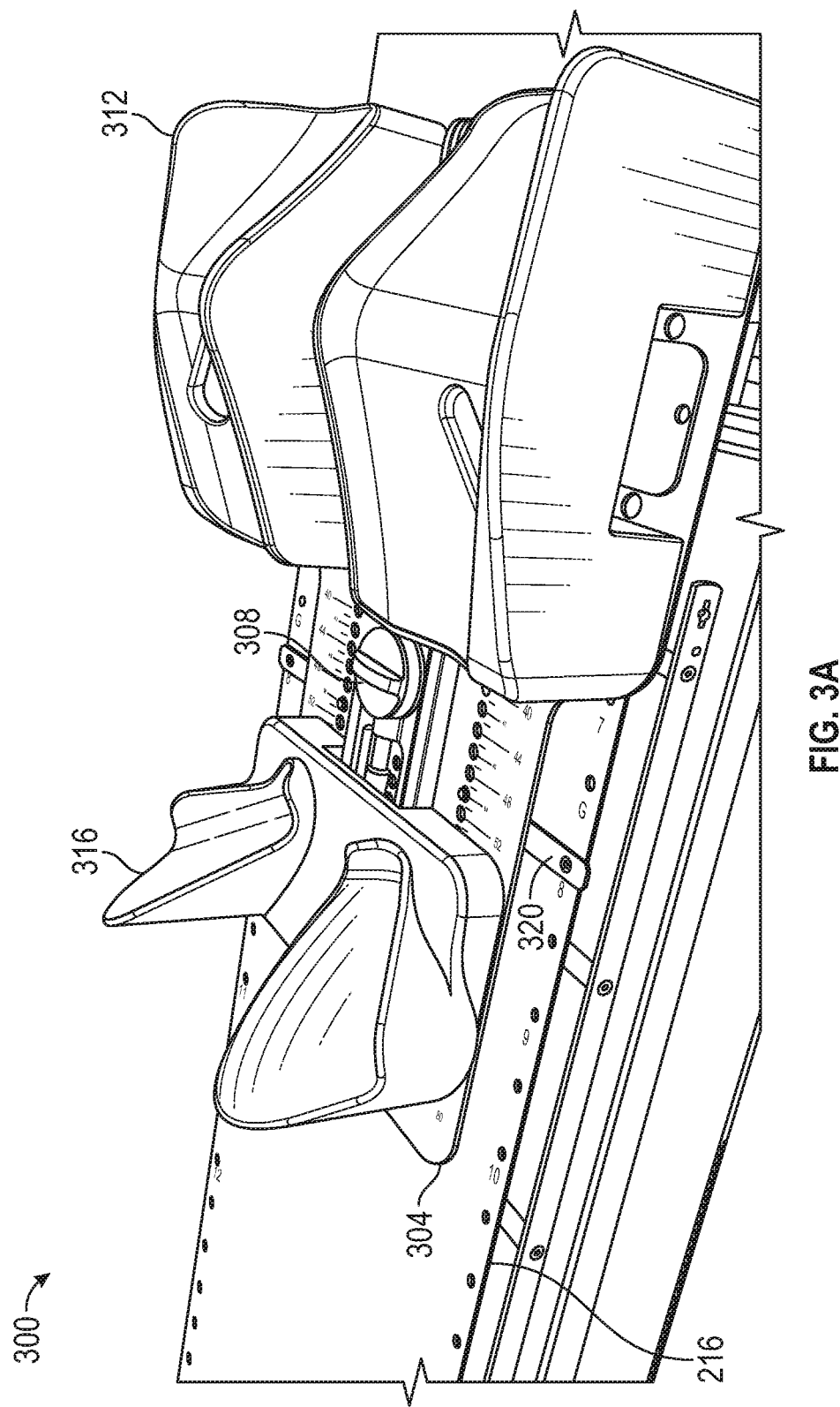
FIGS. 3A and 3B illustrate an example of portions of an ultrasound positioning system.
Figure 3B:
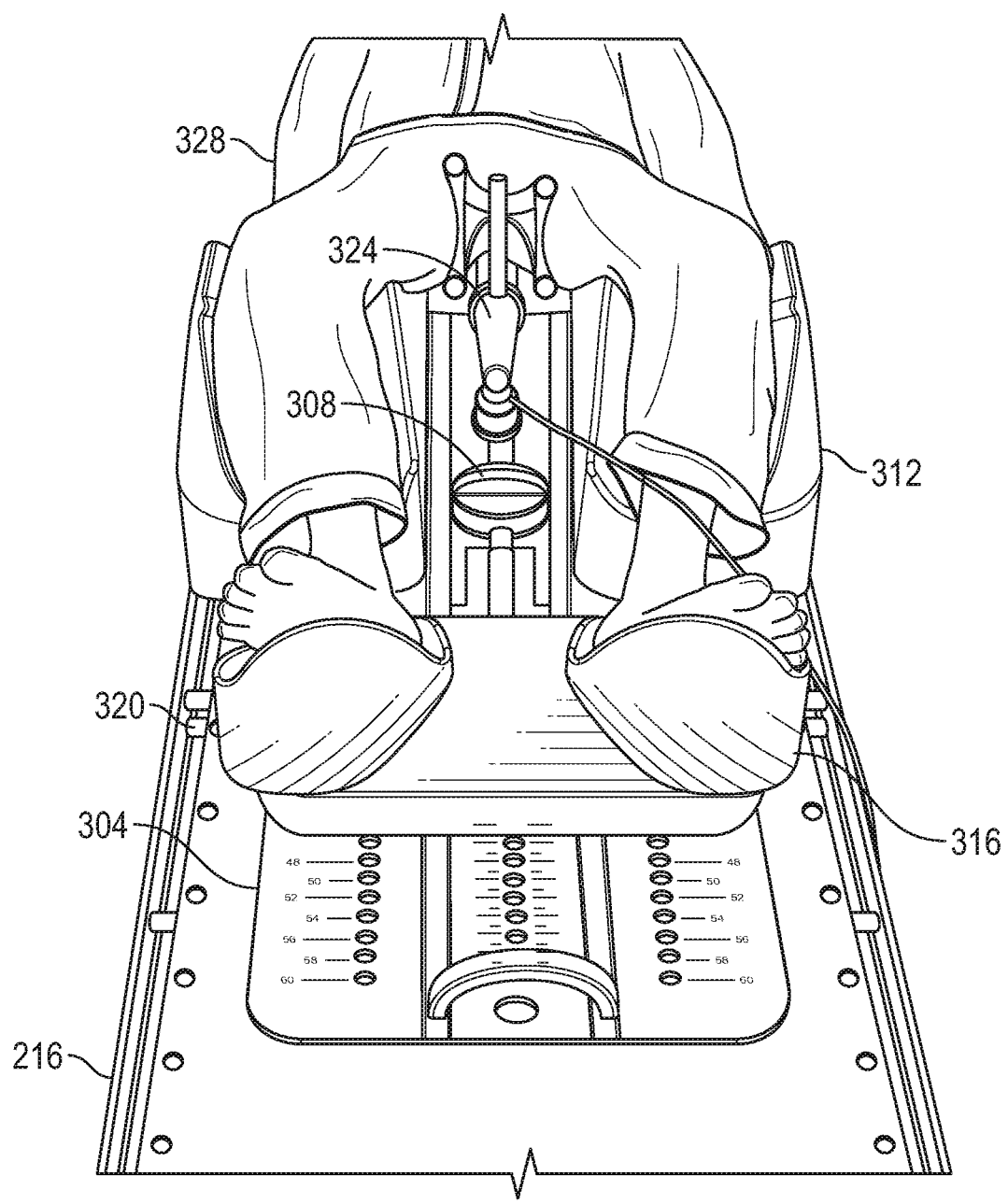

FIG. 3A illustrates an example of portions of an ultrasound positioning system 300. The ultrasound positioning system 300 can include an overlay 304, an ultrasound probe holder 308, knee cushions 312, and ankle cushions 316. One or more portions of the ultrasound positioning system 300 can be directly or indirectly attached to a radiation couch 216, such as via an indexing bar 320 and the overlay 304. The radiation couch 216 can include markings along a longitudinal direction, such as can be used to mark a position of the indexing bar 320, such as with respect to the radiation couch 216. The indexing bar 320 can include reciprocal engagement features or other like mating features, such as on a top and bottom side of the indexing bar 320. The mating features on the bottom side of the indexing bar 320 can be coupled to or engaged with corresponding mating features of the radiation couch 216, such as to selectively position the indexing bar 320 at a marked position with respect to the radiation couch 216. The overlay 304 can include markings and corresponding reciprocal engagement features or other like mating features along a longitudinal direction of the overlay 304. The overlay 304 can be positioned with respect to and engaged or attached to the indexing bar, such as at a desired marked position of the overlay 304. This can include coupling or engaging mating features on a top side of the indexing bar 320 to desired locations of corresponding mating features of the overlay 304. Additionally, the locations of the heels of a patient can be determined using the markings (e.g., ruled markings) of the overlay 304, such as when the patient's ankles are resting flat on the overlay 304. The ultrasound probe holder 308 can be inserted into a central guide region of the overlay 304, such as from a distal edge of the overlay 304 that is located in a direction that is away from the patient's torso. The ultrasound probe holder 308 can include a clamp, which can be used to determine whether the ultrasound probe holder 308 can freely move along a longitudinal direction within the central guide region of the overlay 304, or whether the ultrasound probe holder 308 can be fixed at a particular location along the longitudinal direction. Each of the knee cushions 312 can include a mating feature that can be engaged or coupled to a corresponding mating feature of the overlay 304, such as to fix a position of the knee cushion 312 with respect to the overlay 304. The ankle cushions 316 can be movably coupled to a central guide region of the overlay 304 and can move freely along a longitudinal direction of the overlay 304. An ultrasound probe 324 can be inserted into the ultrasound probe holder 308, such as illustrated in FIG. 3B. A position of the ultrasound probe 324 can then be adjusted, using the ultrasound probe holder 308, such as until the ultrasound probe 324 is brought against or into proximity with a portion of anatomy of a patient 328.

Figure 4:
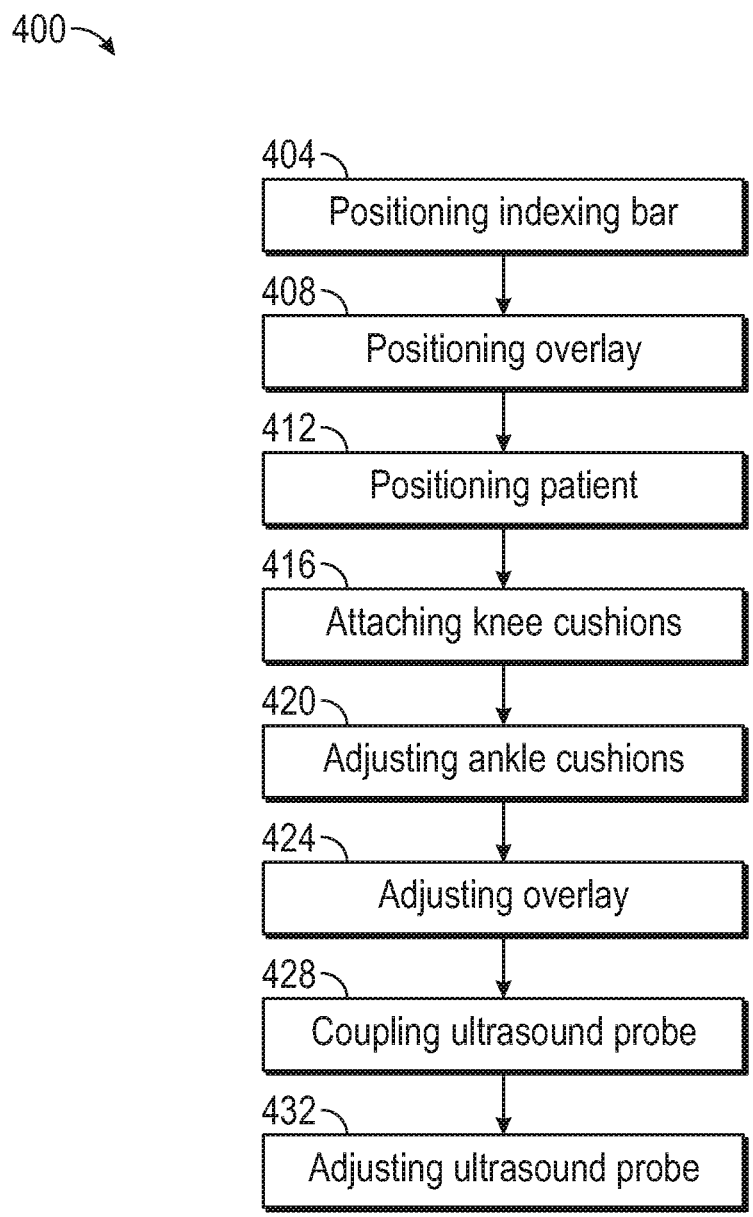
FIG. 4 illustrates an example of a method of using an ultrasound positioning system.

FIG. 4 illustrates an example of portions of a method 400 of using portions of an ultrasound positioning system, such as ultrasound positioning system 300. An indexing bar, such as indexing bar 320, can be positioned at a selected position (e.g., of multiple available indexed positions) on a radiation couch or other platform for radiotherapy, such as couch 216 (step 404). The indexing bar 320 can be selectively placed at a desired marked position of the couch 216. An overlay, such as overlay 304, can be positioned with respect to the indexing bar 320 (step 408). The overlay 304 can be positioned to engage the indexing bar 320 at a marked position of the overlay 304. A patient, such as patient 328, can be positioned overlay 304 on the couch 216 (step 412). In an example, one or more permanent or temporary markings (e.g., tattoos) on the patient can be used to position the patient, such as with respect to the couch 216 and overlay 304. Knee cushions, such as knee cushions 312 can be coupled at a fixed position with respect to the overlay 304 (step 416) A pair of ankle cushions, such as ankle cushions 316 can be adjustably located at a desired position along a longitudinal direction, such as to provide support for the patient's ankles (step 420). A position of the overlay 304 can be adjusted with respect to the couch 216 or the patient 328, such as by adjusting a marked position of the overlay 304 with respect to the indexing bar 320 (step 424). The position of the overlay 304 can be adjusted to provide comfort to the patient 328, such as based on contemporaneous or previous feedback from the patient 328. The marked position of the overlay 304 can be recorded and used in a subsequent radiation therapy session, such as to allow for convenient positioning of the overlay 304 without requiring further adjustments. An ultrasound probe, such as the ultrasound probe 324 can be coupled to the ultrasound probe holder 308 in a central guide region of the overlay 304 (step 428). The ultrasound probe holder 308 can be manually translated (e.g., pushed or pulled by a clinician) in a longitudinal direction towards patient anatomy (e.g., a perineum of the patient) until the ultrasound probe 324 contacts the patient (step 432). The ultrasound probe holder 308 can then be clamped in position. Further (e.g., fine) adjustments of the longitudinal position of the ultrasound probe holder 308 can then be made via a centrally accessible actuator of the ultrasound probe holder 308 (step 436). The further adjustments of the longitudinal position can be used to adjust a pressure exerted on the patient by the ultrasound probe 324. Such fine adjustment can help bring the ultrasound probe close enough against the patient to obtain a good quality image, while limiting the amount of discomfort felt by the patient by the probe pressing against the patient.

Figure 5A:
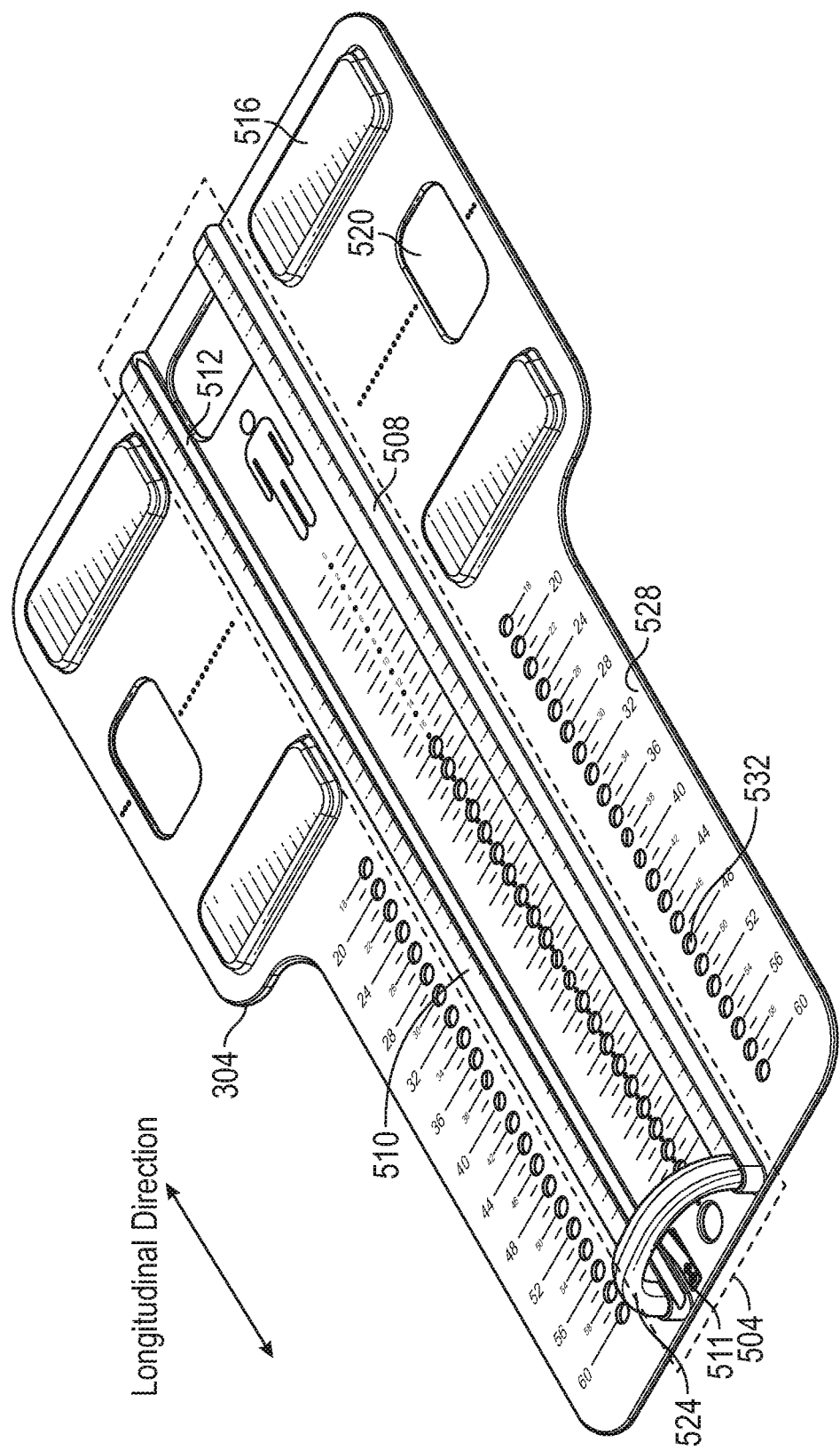
FIGS. 5A and 5B illustrate an example of an overlay.
Figure 5B:
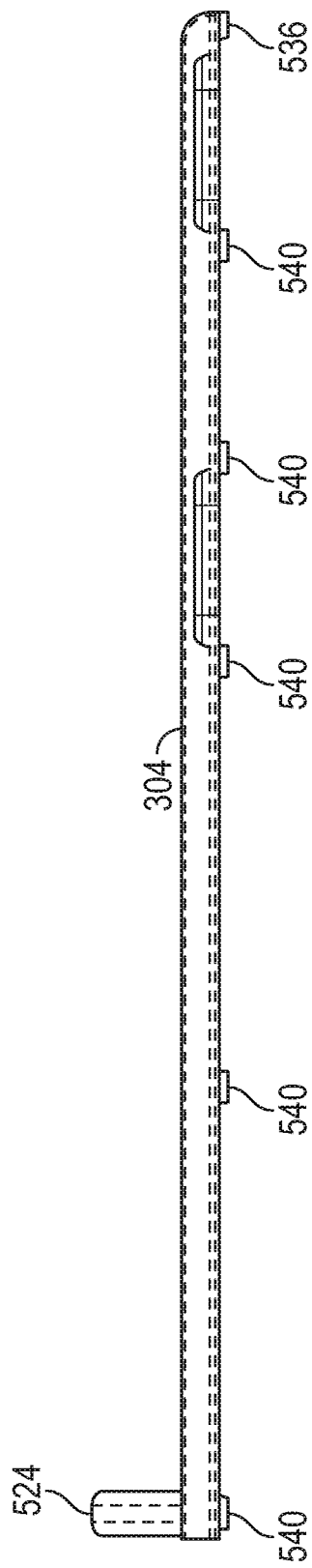

FIG. 5A illustrates an example of an overlay, such as the overlay 304. The overlay 304 can include indexed engagement features 532 such as for coupling the overlay to an indexing bar, such as the indexing bar 320. Each of the engagement features 532 can correspond to at least one corresponding marking 528 of the overlay 304. For example, the corresponding markings can convey information about the spacing between adjacent engagement features 532, or about a cumulative distance from a reference marking and corresponding engagement feature 532. The engagement features 532 can engage directly to a couch, such as couch 216, or indirectly to the couch 216, such as via the indexing bar 320. The overlay 304 can include a central guide region 504, such as indicated by the dashed lines in FIG. 5A. The central guide region 504 can include one or more (e.g., a pair) of guide rails 508. Each of the guide rails 508 can include a V-shaped or other interior (e.g., inward-facing) groove 512 and V-shaped or other exterior (e.g., laterally outward facing) groove 510. The interior grooves 512 can face each other. An ultrasound probe holder, such as the ultrasound probe holder 324 can engage with and can be guided in a longitudinal direction by the interior grooves 512 and a channel therebetween. The overlay 304 can also include a retention feature such as a spring-biased, resiliently-biased, or other flap 511, such as can be configured to allow the probe holder 324 to be inserted into the channel between the interior grooves 512. Inserting the probe holder 324 into the grooves 512 can automatically push the flap out of the way upons such insertion. The flap 511 can then automatically spring outward when the probe holder 324 has been moved along the grooves 512, such as to help prevent the probe holder from being removed from the channel in the absence of manual actuation of the flap 511. Then, when release of the probe holder 324 is desired, the user can depress or otherwise manually actuate the flap 511. The exterior grooves 510 can face outwardly away from each other. Ankle cushions, such as ankle cushions 316 can engage with and can be guided in a longitudinal direction by the exterior grooves 510. The overlay 304 can also include one or more mating features 516 (e.g., one or more protrusions or depressions) that can be coupled to one or more corresponding features of knee cushions, such as on the undersides of the knee cushions 312. The knee cushions can be indexed to the mating features 516. The overlay 304 can also include at least one glide 536 on a bottom side of the overlay 304 as illustrated in FIG. 5B which shows a side view of the overlay 304. In an example, the glide can be formed from a material including polyoxymethylene (POM), also known as acetal. An individual glide 536 can include a protrusion from the bottom of the overlay 304 and can be made of a hard plastic or other material having a relatively low coefficient of friction with the couch 216. The at least one glide 536 can allow the overlay 304 to easily slide back and forth on the couch 216. The overlay 304 can also include at least one sticky bump 540. An individual sticky bump 540 can include a protrusion from the bottom of the overlay 304 and can be made of a soft plastic or other material having a relatively large coefficient of friction with the couch 216. In an example, the sticky bump can be formed from a material including polyurethane (PUR) or synthetic rubber. The at least one sticky bump 540 can be configured to provide resistance to sliding movement of the overlay 304 when the at least one sticky bump 540 is in contact with the couch 216. The overlay 304 can also include a handle 524 that can be used to elevate an inferior end (e.g., end of overlay further from the patient's head) of the overlay 304 where the handle 524 is located. When the handle 524 is elevated, the at least one sticky bump 540 can be brought out of contact with the couch 216, while the at least one glide 536 can remain in contact with the couch 216. Then, with only the at least one glide 536 in contact with the couch 216, the overlay 304 can be repositioned. The handle 524 can then be lowered to bring the at least one sticky bump 540 back into contact with the couch 216.

Figure 6:
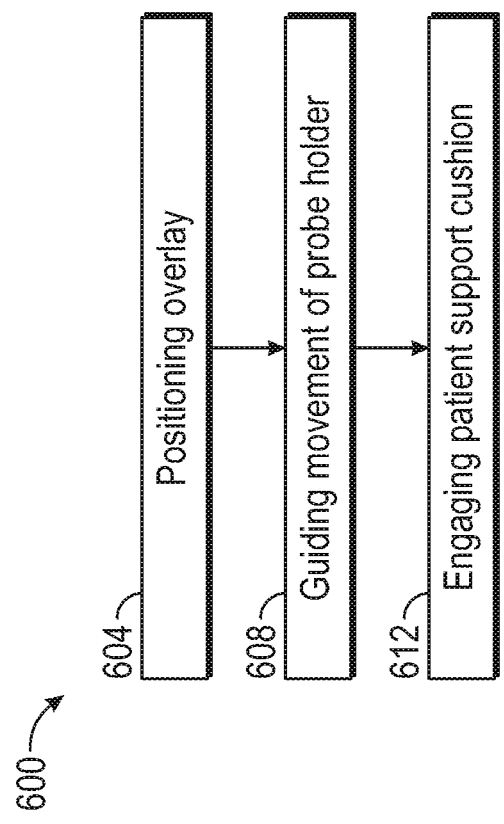
FIG. 6 illustrates an example of portions of method of using an overlay.

FIG. 6 illustrates a method 600 of using an overlay, such as the overlay 304. The overlay can be positioned at an indexed position on a couch, such as couch 216 (step 604). The overlay 304 can guide translational movement of an ultrasound probe holder, such as the ultrasound probe holder 308, along a longitudinal axis of the overlay from within a central region of the overlay (step 608). A longitudinal groove, such as one or both of the interior grooves 512 can be used to guide the translational movement of the ultrasound probe holder. One or more patient support cushions can be engaged using one or more longitudinal grooves, such as the exterior grooves 510 of the overlay (step 612). One or more patient support cushions can also be engaged to one or more mating features (e.g., protrusions or depressions) on a top surface of the overlay 304. The overlay can be initially positioned or re-positioned without indexed engagement using a handle and one or more glides, such as the handle 524 the at least one glide 536. After being positioned, the overlay can be placed into engagement with one or more indexed engagement features, such as one or more mating features of an indexing bar, such as the indexing bar 320.

Figure 7A:
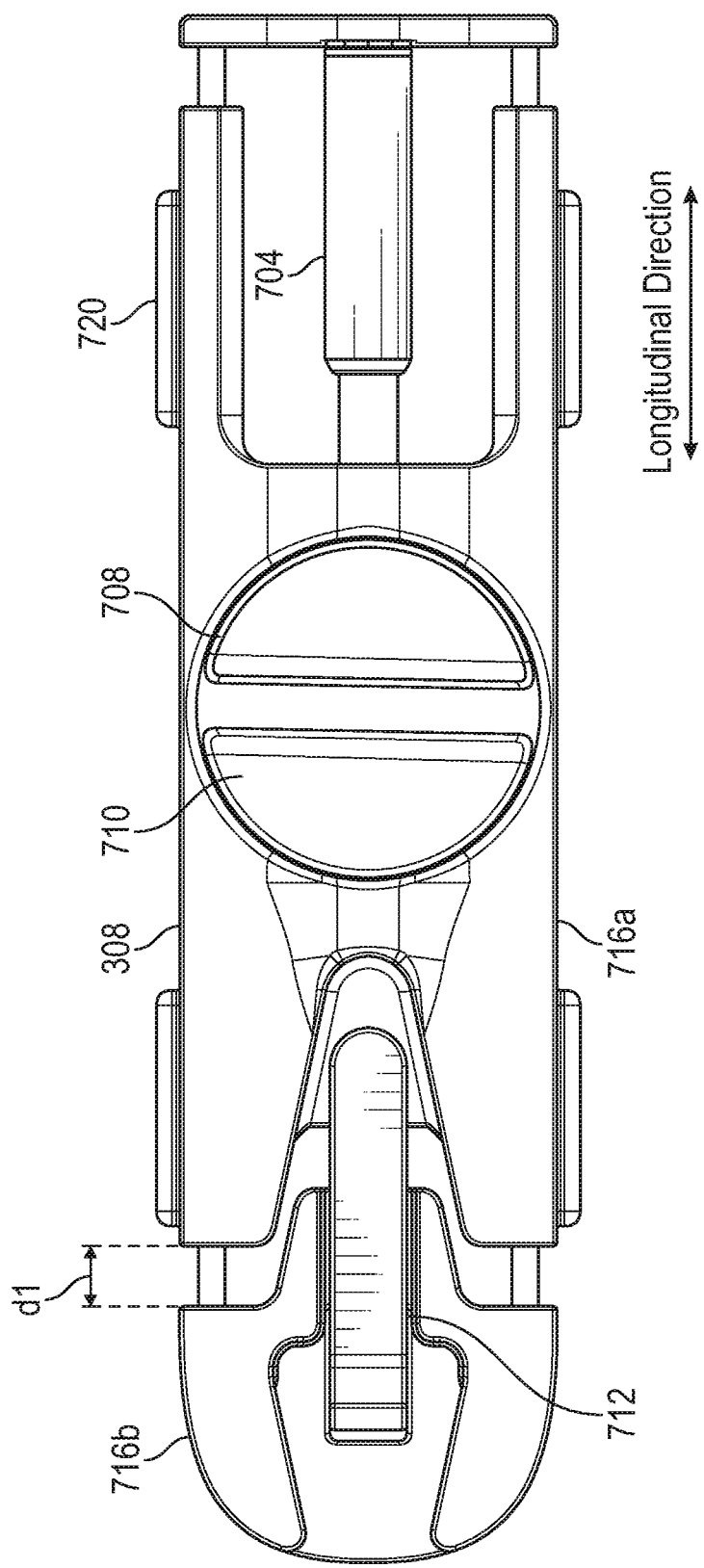
FIG. 7A illustrates an example of portions of an ultrasound probe holder.
Figure 7B:
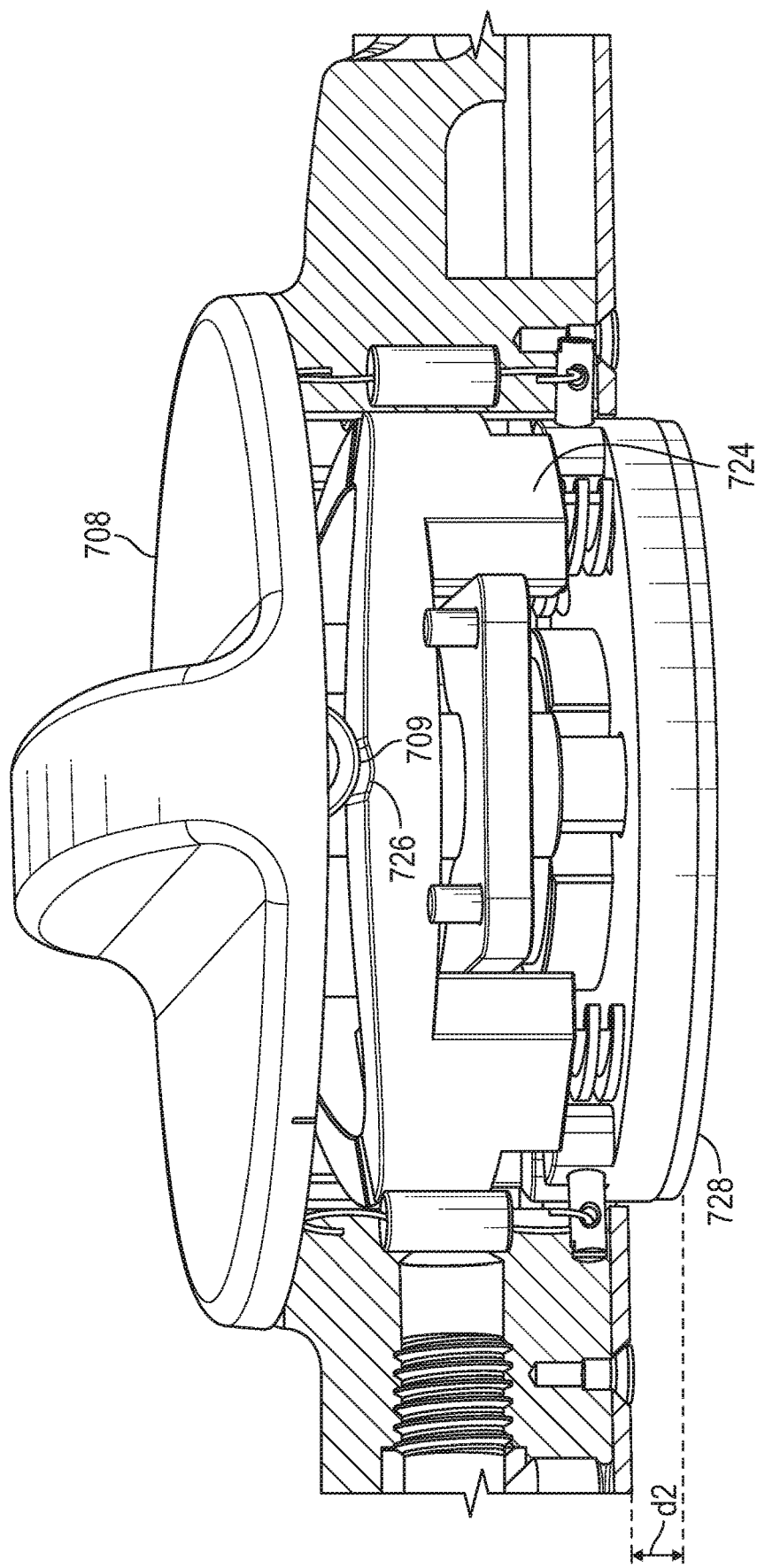
FIGS. 7B and 7C illustrate an example of portions of a clamping mechanism in an ultrasound probe holder.
Figure 7C:
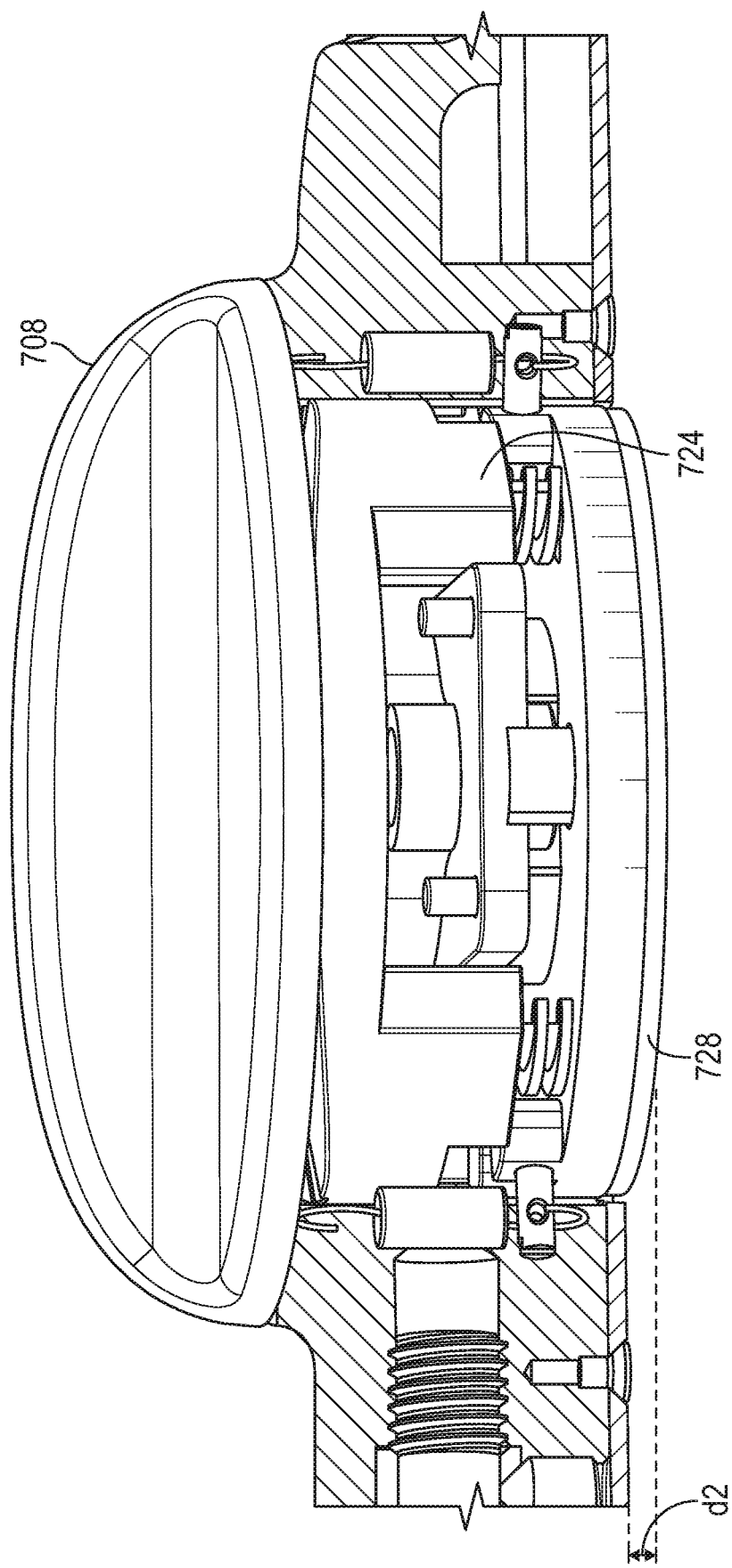

FIG. 7A illustrates an example of an ultrasound probe holder, such as the ultrasound probe holder 308. The ultrasound probe holder 308 can include a clamp 708, a fine adjustment mechanism 704, a retractable flap 712, a first body portion 716a, a second body portion 716b, and protrusions 720. The retractable flap 712 can lock an ultrasound probe, such as the ultrasound probe 324 into position when the ultrasound probe is coupled to the second body portion 716b. The retractable flap 712 can be manually actuated to release the ultrasound probe 324 from the second body 716b. The protrusions 720 can include outwardly facing protrusions aligned along a longitudinal direction. The protrusions 720 can interface with corresponding longitudinal grooves of an overlay, such as the interior grooves 512, such as to allow the ultrasound probe holder 308 to be translated within a central guide region of the overlay 304 in a longitudinal direction. In an example, the protrusions 720 can have a semi-circular cross section and the interior grooves 512 can have a v-shaped cross section that can accommodate the protrusions 720. The clamp 708 can be centrally located within the ultrasound probe holder and can include a rotatable knob 710, a disc 724, and a plate 728 such as illustrated in FIGS. 7B-7C. One or more springs and associated mechanical linkage can be used to maintain contact between the disc 724 and the rotatable knob 710, even as the rotatable knob 710 is rotated between different positions. At least one roller 709 can be attached to an underside of the knob 710. The at least one roller 709 can slide along the disc 724 when the knob 710 is rotated. The disc can include at least one notched portion 726 that can be shaped to accommodate the at least one roller 709. A position of the knob 710 can be locked (e.g., held in place in the absence of manual rotation of the knob 710) when the at least one roller 709 is resting in the at least one notched portion 726.

In an example, the clamp 708 can include two rollers 709) that can be diametrically opposing to one another. The disc 724 can include four notches 726 spaced at ninety degree intervals along the disc 724. A first pair of the four notches 726 can be spaced by one hundred and eighty degrees and can correspond to a first height. A second pair of the four notches 726 can be spaced by one hundred and eighty degrees and can correspond to a second height. When the two rollers 709 engage with the first pair of the four notches 726 (a first knob position), such as can be illustrated in FIG. 7B, the disc 728 can extend from a bottom of the ultrasound probe holder 308 by a first distance $d_2$, such as can provide a clamping force to lock the ultrasound probe holder 308 in place with respect to the overlay 304. The clamping force can be provided by a frictional force between the disc 728 and the overlay 304. The disc 728 can include a relatively sticky substance (e.g., polyurethane (PUR) or synthetic rubber) on a surface to provide increased friction between the disc 728 and the overlay 304. Additional clamping force can be provided by the protrusions 720 being brought into closer contact with the interior grooves 512 when the disc 728 extends from the bottom of the ultrasound probe holder 308 by the first distance $d_2$. When the two rollers 709 engage with the second pair of the four notches 726 (a second knob position), such as can be illustrated in FIG. 7C, the disc 728 can extend from a bottom of the ultrasound probe holder 308 by a second distance $d_2$ smaller than the first distance $d_1$, such as can reduce a clamping force to allow the ultrasound probe holder 308 to move freely in a longitudinal direction with respect to the overlay 304. Additionally, a clearance between the protrusions 720 and the interior grooves 512 can be increased when the two rollers 709 engage with the second pair of the four notches 726. Thus, by toggling between the first and second knob positions, the ultrasound probe holder 308 can be clamped or unclamped to the overlay 304.

The fine adjustment mechanism 704 can include a rotatable knob that can be centrally accessed when the patient is resting on the overlay 304 and radiation couch 216 as illustrated in FIG. 3B (e.g., the fine adjustment mechanism can be accessed from a central region of the overlay 304, and need not be accessed laterally from the side). The rotatable knob can be actuated, such as to adjust a distance between the first body portion 716a and the second body portion 716b. In an example where an ultrasound probe, such as the ultrasound probe 324 can be mounted to the second body portion 716b, a position of the ultrasound probe can be adjusted with respect to the overlay 304 by using actuating the rotatable knob of the fine adjustment mechanism 704. The rotatable knob can be turned in a first direction, such as to cause the first body portion 716a to move away from the second body portion 716b, such as to increase a distance $d_1$ between the first body portion 716a and 716b. The rotatable knob can also be turned in a second direction different from the first direction, such as to cause the first body portion 716a to move toward the second body portion 716b, such as to decrease a distance $d_1$ between the first body portion 716a and 716b The rotatable knob can adjust the distance $d_1$ between the first body portion 716a and 716b independent of whether the ultrasound probe holder 308 is clamped to the overlay 304.

Figure 8:
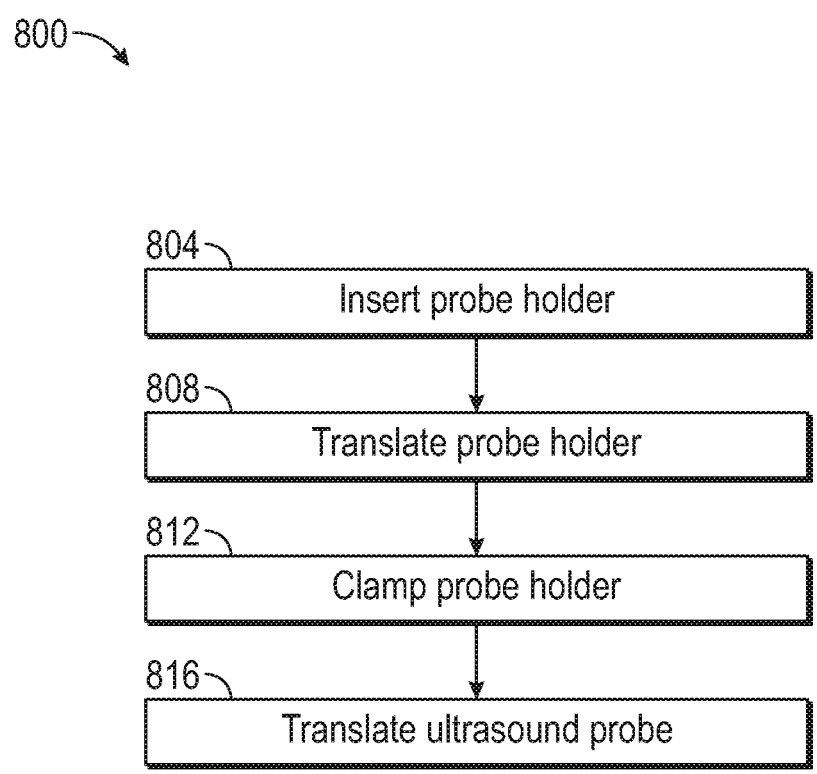
FIG. 8 illustrates an example of portions of a method of using an ultrasound probe holder.

FIG. 8 illustrates an exemplary method 800 of using an ultrasound probe holder. The probe holder can be inserted into a central guide region of an overlay, such as the overlay 304 (step 804). The ultrasound probe holder can be automatically engaged to the overlay upon insertion onto a longitudinal path in a central guide region of the overlay 304. The probe holder can be user-accessed and user-controlled from within a central region to translate the probe longitudinally toward or away from patient anatomy (step 808). The probe holder can be clamped at a specified location along the longitudinal translation path (step 812). The clamping can reduce a clearance within a groove, such as an interior groove 512. An actuator on the clamp can be rotated to increase a frictional force associated with the probe holder. The actuator can be rotated in a first direction to provide clamping of the ultrasound probe holder 308 to the overlay 304. The actuator can then be further rotated in the first direction or rotated in a second direction opposite to the first direction to reduce clamping of the ultrasound probe holder 308 to the overlay 304. An ultrasound probe, such as the ultrasound probe 324 can then be attached to the ultrasound probe holder. The ultrasound probe can be attached a portion of the ultrasound probe holder and can be locked into place by a retractable flap. The ultrasound probe 324 can be further translated along a longitudinal direction, such as by using a centrally located and centrally accessible fine adjustment mechanism, such as the fine adjustment mechanism 704 (step 816).

Figure 9A:
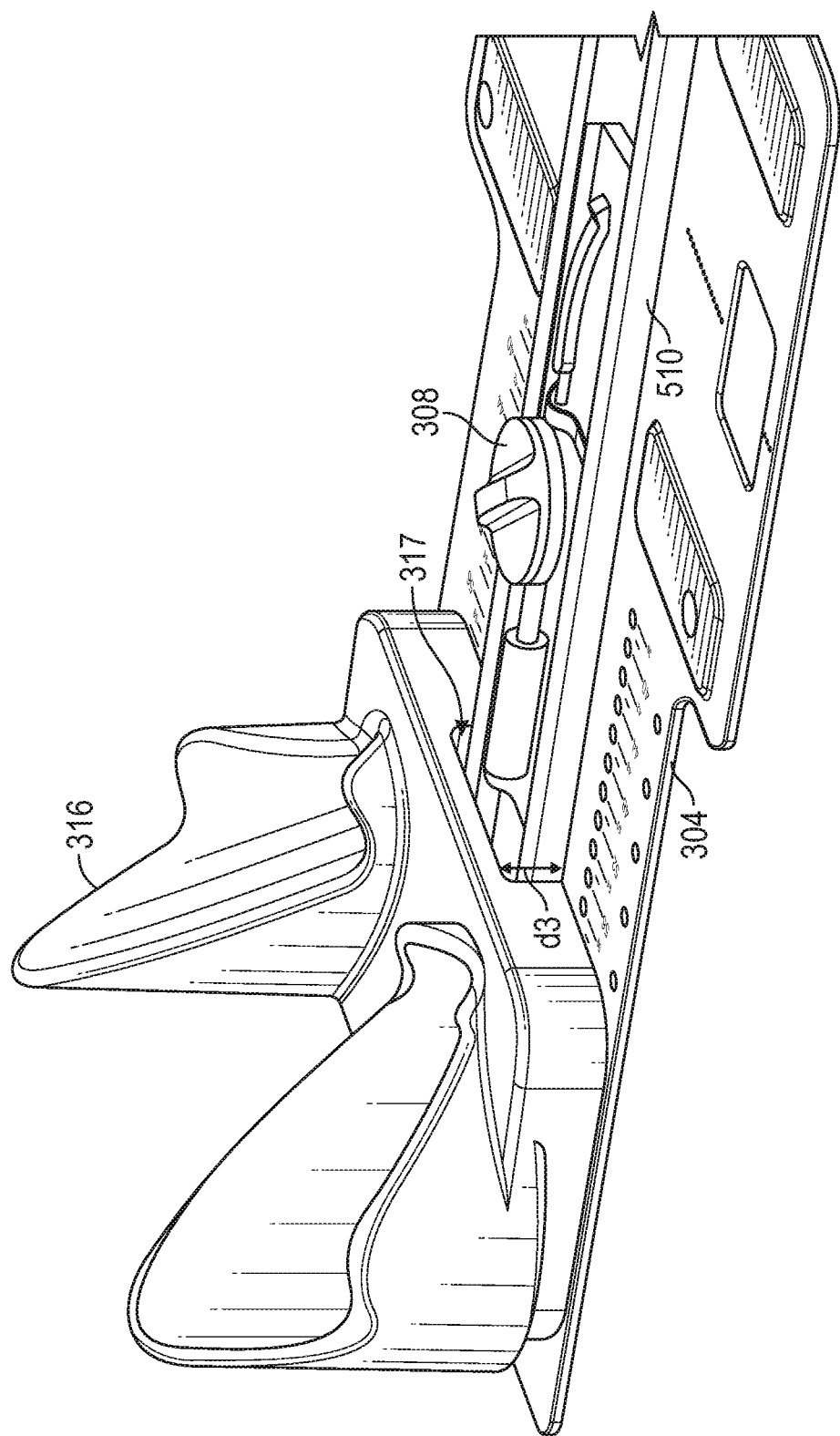
Figure 9B:
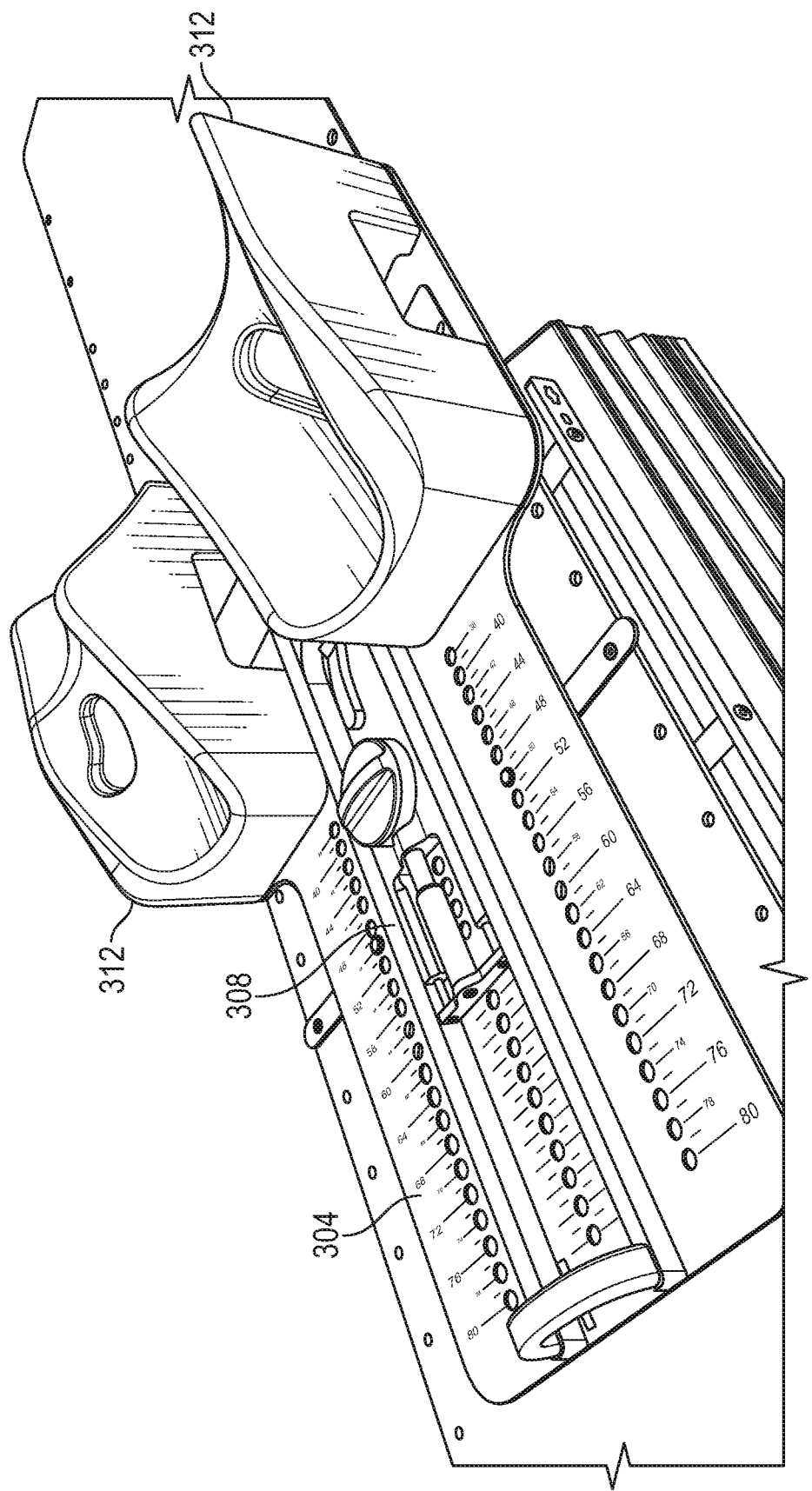
Figure 9C:
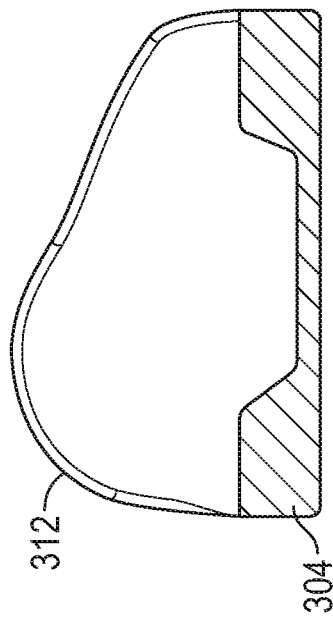
Figure 9C:
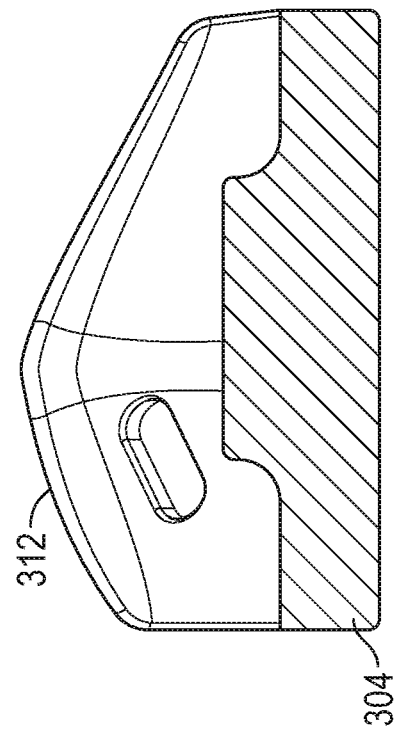
Figure 9D:
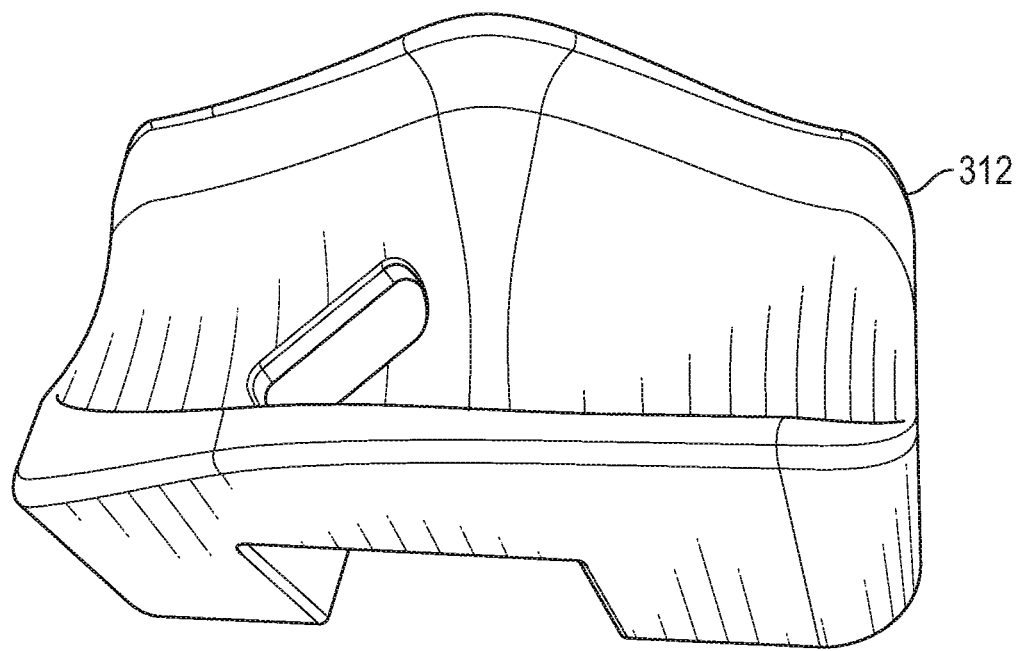
Figure 9E:
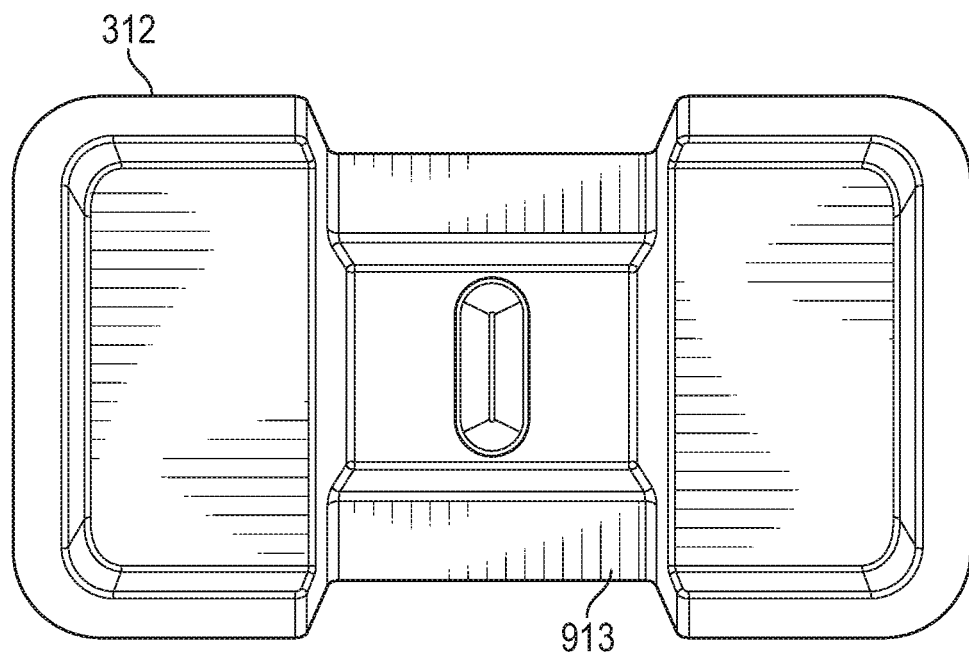
Figure 9F:
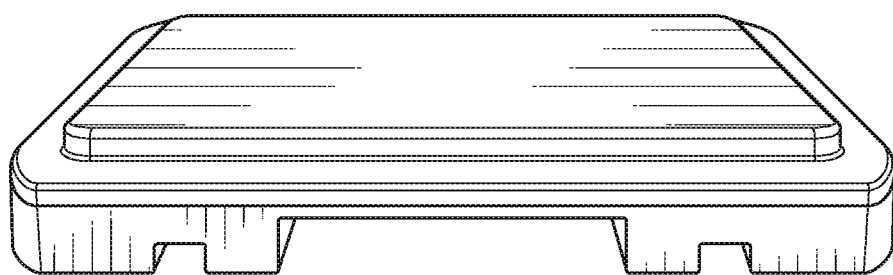
Figure 9G:
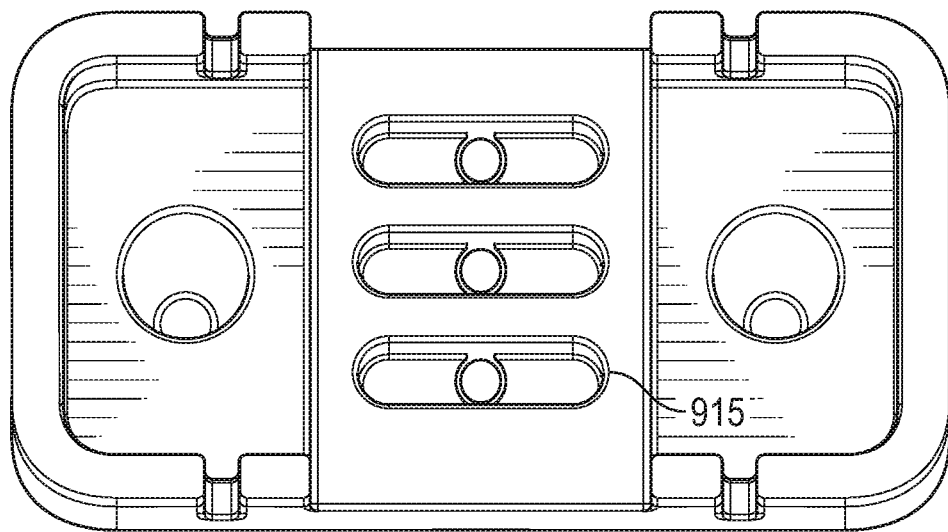

FIGS. 9A and 9B illustrate examples of a patient support cushions, such as ankle cushions 316 and knee support cushions 312. The knee support cushions 312 can include portions shaped to accommodate a patient's knee from behind the knee. Additionally, the knee support cushions 312 can be shaped and arranged to provide a space therebetween that can accommodate an ultrasound probe holder, such as ultrasound probe holder 308. Thus, the ultrasound probe holder 308 can freely slide between the knee support cushions 312 in a central guide region of the overlay 304. As illustrated in FIG. 9C, the knee support cushions can include a recessed mounting portion that includes indexed engagement features for engaging a corresponding raised mounting portion of an overlay, such as overlay 304. The knee support cushions can also include a raised mounting portion that includes indexed engagement features for engaging a corresponding recessed mounting portion of an overlay, such as overlay 304. The knee support cushions can be indexed to the overlay in a longitudinal and/or lateral direction. The space provided between the knee support cushions can allow for access to a patient's perineum. A booster can be shaped to be inserted between an individual one of the knee support cushions and the overlay, such as to adjust a height of the individual knee support cushion. The ankle cushions 316 can include a lateral slide for engaging a corresponding feature of an overlay, such as the overlay 304. A bottom side of the ankle cushions can include a recessed portion 317 that can provide a space to accommodate an ultrasound probe holder, such as the ultrasound probe holder 308. The recessed portion 317 can include slides that can engage with at least one exterior groove, such as exterior groove 510 of the overlay. The ankle cushions 316 can then be translated in a longitudinal direction along the overlay 304. The recessed portion 317 can have a height d3 that can accommodate the height of the ultrasound probe holder, such that the ultrasound probe holder can slide underneath the ankle cushions, or vice versa. In an example, the recessed portions can have a height d3 that can accommodate only a portion of the height of the ultrasound probe holder, such that only a portion of the ultrasound probe holder can slide underneath the ankle cushions. For example, the height d3 may not be large enough to accommodate a knob of the ultrasound probe holder, such that the knob of the ultrasound probe holder acts as a stop to limit relative longitudinal translation between the knee cushions and the ultrasound probe holder. Additionally, each of the individual knee support cushions 312 can include a handle 913 on an underside of the individual knee support cushion 312 as shown in FIGS. 9D and 9E. The handle 913 can include a protrusion shaped to be gripped by a human hand. The handle 913 can be shaped such as to provide ease of grabbing the knee support cushion 312 with a single hand. This can be useful for a therapist when setting up the patient on the radiation couch. For example, one hand can be used to lift the patient's leg while the other hand can be used to insert the knee support cushion 312. A similar handle 915 can be included on an underside of a booster as shown in FIGS. 9F and 9G. The handle 915 can include recessed portions that can be gripped by fingers of a clinician or therapist. The various recessed portions can be spaced and arranged to accommodate different hand sizes. A similar handle 917 can be included on an underside of the ankle cushions 316 as illustrated in FIGS. 9H and 91. The handle 917 can include recessed portions that can be gripped by fingers of a clinician or therapist. The various recessed portions can be spaced and arranged to accommodate different hand sizes.

Figure 10:
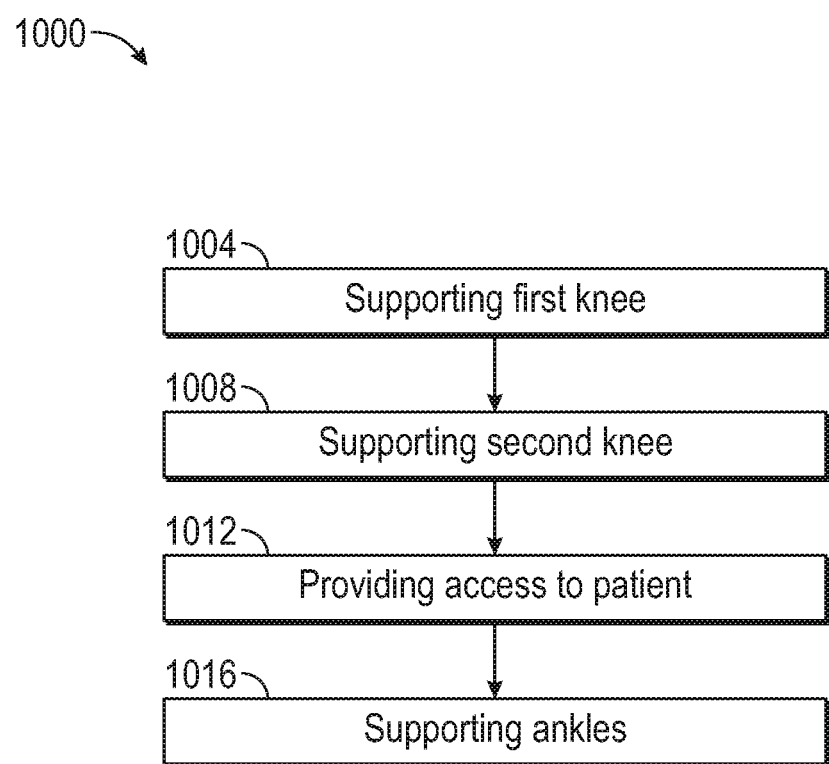
FIG. 10 illustrates an example of a method of using one or more patient support cushions.

FIG. 10 illustrates a method of using patient support cushions, such as knee cushions 312 and ankle cushions 316. A first knee cushion 312 can be used to support a patient's first knee from behind the knee (step 1004). A second knee cushion 312 can be used to support a patient's second knee from behind the knee (step 1008). The first and second knee cushions can provide access to a patient via a probe holder in a central region formed by the first and second knee cushions being placed in lateral regions on opposing sides. Each of the individual knee cushions can be indexed to an overlay, such as the overlay 304. An ankle cushion can be used to support the patient's ankles from behind the ankles (step 1012). The ankle cushion can be translated in a longitudinal direction along a longitudinal track. A booster can be provided between an individual one of the knee cushions and the overlay, such as to adjust a height of the individual knee cushion. The booster can also be used between the ankle cushion and the overlay, such as to adjust a height of the ankle cushion.

ADDITIONAL NOTES

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document, for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

Embodiments of the invention may be implemented with computer-executable instructions. The computer-executable instructions (e.g., software code) may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CDROMS, magnetic-optical disks, removable optical disks (e.g., compact disks and digital video disks), flash memory devices, magnetic cassettes, memory cards or sticks (e.g., secure digital cards), random access memories (RAMs) (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the invention, the method of creating a component or module can be implemented in software, hardware, or a combination thereof. The methods provided by various embodiments of the present invention, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplar) embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A probe holder for positioning an ultrasound probe, the probe holder comprising:
    a probe holder body, configured to be coupled to, to translate longitudinally within, and to be user-accessed and user-controlled from within, a central region of a radiation couch or overlay thereupon, the central region of the radiation couch or overlay being located between lateral regions that are arranged to be underlying a subject's legs; and
    a clamp located within a central portion of the probe holder body, the clamp configured to localize the probe holder at a specified location along a translation path in the central region of the radiation couch or overlay,
    wherein the clamp includes a rotatably-actuated clamp located within a central portion of the probe holder body, the clamp being configured to increase a frictional force between the probe holder body and the overlay to localize the probe holder at a specified location along a translation path in the central region of the radiation couch or overlay.

2. The probe holder of claim 1 comprising transversely outwardly facing protrusions aligned along a longitudinal direction, the outwardly facing protrusions configured to interface with corresponding longitudinal grooves of the overlay to provide for adjustment of the probe body along the longitudinal direction.

3. The probe holder of claim 1 comprising transversely outwardly facing hemispherical protrusions having a semi-circular cross-section aligned along a longitudinal direction, the outwardly facing protrusions configured to interface with corresponding longitudinal v-grooves of the overlay to provide for adjustment of the probe body along the longitudinal direction.

4. The probe holder of claim 1 comprising a retractable flap configured to hold the ultrasound probe in place upon the ultrasound probe engaging with the probe holder and release the ultrasound probe upon being actuated by a user.

5. The probe holder of claim 1 comprising a rotatable knob located within the central portion of the probe holder body, the rotatable knob being configured to apply a force to the overlay when engaging a relatively elevated portion of a disc below the rotatable knob to provide an outwardly facing protrusion.

6. The probe holder of claim 5, wherein the rotatable knob is configured to decrease a clearance between outwardly facing protrusions of the probe holder and corresponding longitudinal grooves of the overlay in response to a rotation in a first direction.

7. The probe holder of claim 6, wherein the rotatable knob is configured to increase a clearance between outwardly facing protrusions of the probe holder and corresponding longitudinal grooves of the overlay in response to further rotation in the first direction.

8. The probe holder of claim 6, wherein the rotatable knob is configured to increase a clearance between outwardly facing protrusions of the probe holder and corresponding longitudinal grooves of the overlay in response to a rotation in a second direction opposite to the first direction.

9. The probe holder of claim 1 comprising a rotatable, longitudinally aligned member configured to longitudinally translate the ultrasound probe with respect to the overlay and to be user-accessed and user-controlled from within, a central region of a radiation couch or overlay thereupon.

10. The probe holder of claim 9 wherein the rotatable, longitudinally aligned member is located on a side opposite of the ultrasound probe to provide for access to the rotatable, longitudinally aligned member and is located to be user-accessed and user-controlled from within, a central region of a radiation couch or overlay thereupon.

* * * * *